(12) United States Patent
Baily

(10) Patent No.: US 7,160,299 B2
(45) Date of Patent: Jan. 9, 2007

(54) METHOD OF FUSING BIOMATERIALS WITH RADIOFREQUENCY ENERGY

(75) Inventor: Ali Baily, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 235 days.

(21) Appl. No.: 10/833,989

(22) Filed: Apr. 28, 2004

(65) Prior Publication Data

US 2005/0021026 A1    Jan. 27, 2005

Related U.S. Application Data

(60) Provisional application No. 60/467,181, filed on May 1, 2003.

(51) Int. Cl.
*A61B 18/18* (2006.01)

(52) U.S. Cl. ......................... 606/51; 128/898

(58) Field of Classification Search ........ 606/205–221, 606/51; 128/898
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |

(Continued)

FOREIGN PATENT DOCUMENTS

CA    2104423    2/1994

(Continued)

OTHER PUBLICATIONS

PCT/US01/11340, International Search Report.

(Continued)

*Primary Examiner*—Roy D. Gibson
*Assistant Examiner*—Pete Vrettakos

(57) ABSTRACT

A method of fusing biomaterial and tissue using radiofrequency energy includes the steps of: providing a vessel sealing instrument having opposing jaw members which are movable relative to one another to compress tissue therebetween. The vessel sealing instrument includes at least one stop member affixed thereto for regulating the distance between the opposing jaw members. The method also includes the steps of: providing a biomaterial; positioning the biomaterial in abutting relation to tissue; approximating the biomaterial and tissue between the jaw members; compressing the biomaterial and tissue between the jaw members under a working pressure within the range of about 3 $kg/cm^2$ to about 16 $kg/cm^2$; and energizing the jaw members with radiofrequency energy to effectively fuse the biomaterial and the tissue such that the biomaterial and the tissue reform into a single, fused mass.

9 Claims, 16 Drawing Sheets
(4 of 16 Drawing Sheet(s) Filed in Color)

U.S. PATENT DOCUMENTS

| | | |
|---|---|---|
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,667,526 A | 9/1997 | Levin |
| 5,674,220 A | 10/1997 | Fox et al. |
| 5,681,282 A | 10/1997 | Eggers et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |

| | | | | | | |
|---|---|---|---|---|---|---|
| 5,766,170 | A | 6/1998 | Eggers | H1904 | H | 10/2000 | Yates et al. |
| 5,769,849 | A | 6/1998 | Eggers | 6,126,658 | A | 10/2000 | Baker |
| 5,776,128 | A | 7/1998 | Eggers | 6,152,923 | A | 11/2000 | Ryan |
| 5,776,130 | A | 7/1998 | Buysse et al. | 6,174,309 | B1 | 1/2001 | Wrublewski et al. |
| 5,779,701 | A | 7/1998 | McBrayer et al. | 6,179,834 | B1 | 1/2001 | Buysse et al. |
| 5,792,137 | A | 8/1998 | Carr et al. | 6,179,837 | B1 | 1/2001 | Hooven |
| 5,792,177 | A | 8/1998 | Kaseda | 6,183,467 | B1 | 2/2001 | Shapeton et al. |
| 5,797,938 | A | 8/1998 | Paraschac et al. | 6,187,003 | B1 | 2/2001 | Buysse et al. |
| 5,797,958 | A | 8/1998 | Yoon | 6,190,386 | B1 | 2/2001 | Rydell |
| 5,800,449 | A | 9/1998 | Wales | 6,193,718 | B1 | 2/2001 | Kortenbach et al. |
| 5,810,808 | A | 9/1998 | Eggers | 6,206,876 | B1 | 3/2001 | Levine et al. |
| 5,810,811 | A | 9/1998 | Yates et al. | 6,206,877 | B1 | 3/2001 | Kese et al. |
| 5,810,877 | A | 9/1998 | Roth et al. | 6,224,593 | B1 | 5/2001 | Ryan et al. |
| 5,814,043 | A | 9/1998 | Shapeton | 6,228,080 | B1 | 5/2001 | Gines |
| 5,817,093 | A | 10/1998 | Williamson, IV et al. | 6,228,083 | B1 | 5/2001 | Lands et al. |
| 5,820,630 | A | 10/1998 | Lind | 6,257,241 | B1 | 7/2001 | Wampler |
| 5,827,271 | A | 10/1998 | Buysse et al. | 6,267,761 | B1 | 7/2001 | Ryan |
| 5,827,279 | A | 10/1998 | Hughett et al. | 6,270,497 | B1 | 8/2001 | Sekino et al. |
| 5,827,281 | A | 10/1998 | Levin | 6,270,508 | B1 | 8/2001 | Klieman et al. |
| 5,833,690 | A | 11/1998 | Yates et al. | 6,273,887 | B1 | 8/2001 | Yamauchi et al. |
| 5,843,080 | A | 12/1998 | Fleenor et al. | 6,277,117 | B1 | 8/2001 | Tetzlaff et al. |
| 5,849,022 | A | 12/1998 | Sakashita et al. | 6,280,458 | B1 | 8/2001 | Boche et al. |
| 5,853,412 | A | 12/1998 | Mayenberger | 6,283,961 | B1 | 9/2001 | Underwood et al. |
| 5,876,401 | A | 3/1999 | Schulze et al. | 6,287,344 | B1 | 9/2001 | Wampler et al. |
| 5,891,141 | A | 4/1999 | Rydell | D449,886 | S | 10/2001 | Tetzlaff et al. |
| 5,891,142 | A | 4/1999 | Eggers et al. | 6,322,561 | B1 | 11/2001 | Eggers et al. |
| 5,893,863 | A | 4/1999 | Yoon | 6,334,860 | B1 | 1/2002 | Dorn |
| 5,893,875 | A | 4/1999 | O'Connor et al. | 6,334,861 | B1 | 1/2002 | Chandler et al. |
| 5,893,877 | A | 4/1999 | Gampp, Jr. et al. | 6,350,264 | B1 | 2/2002 | Hooven |
| 5,902,301 | A | 5/1999 | Olig | 6,352,536 | B1 | 3/2002 | Buysse et al. |
| 5,906,630 | A | 5/1999 | Anderhub et al. | 6,372,228 | B1 | 4/2002 | Gregory |
| 5,908,420 | A | 6/1999 | Parins et al. | D457,958 | S | 5/2002 | Dycus et al. |
| 5,913,874 | A | 6/1999 | Berns et al. | D457,959 | S | 5/2002 | Tetzlaff et al. |
| 5,921,984 | A | 7/1999 | Sutcu et al. | 6,387,094 | B1 | 5/2002 | Eitenmuller |
| 5,935,126 | A | 8/1999 | Riza | 6,398,779 | B1 | 6/2002 | Buysse et al. |
| 5,944,718 | A | 8/1999 | Dafforn et al. | 6,402,747 | B1 | 6/2002 | Lindemann et al. |
| 5,951,549 | A | 9/1999 | Richardson et al. | 6,409,728 | B1 | 6/2002 | Ehr et al. |
| 5,954,720 | A | 9/1999 | Wilson et al. | H2037 | H | 7/2002 | Yates et al. |
| 5,961,514 | A | 10/1999 | Long et al. | 6,416,486 | B1 | 7/2002 | Wampler |
| 5,972,007 | A | 10/1999 | Sheffield et al. | 6,419,675 | B1 | 7/2002 | Gallo, Sr. |
| 5,976,132 | A | 11/1999 | Morris | 6,425,896 | B1 | 7/2002 | Baltschun et al. |
| 5,984,939 | A | 11/1999 | Yoon | 6,443,970 | B1 | 9/2002 | Schulze et al. |
| 5,989,244 | A | 11/1999 | Gregory et al. | 6,451,018 | B1 | 9/2002 | Lands et al. |
| 5,989,277 | A | 11/1999 | LeMaire, III et al. | 6,458,128 | B1 | 10/2002 | Schulze |
| 5,990,379 | A | 11/1999 | Gregory | 6,458,130 | B1 | 10/2002 | Frazier et al. |
| 6,004,333 | A | 12/1999 | Sheffield et al. | 6,464,704 | B1 | 10/2002 | Schmaltz et al. |
| 6,004,335 | A | 12/1999 | Vaitekunas et al. | 6,503,248 | B1 | 1/2003 | Levine |
| 6,010,516 | A | 1/2000 | Hulka et al. | 6,506,189 | B1 | 1/2003 | Rittman, III et al. |
| 6,024,741 | A | 2/2000 | Williamson et al. | 6,508,815 | B1 | 1/2003 | Strul et al. |
| 6,024,744 | A | 2/2000 | Kese et al. | 6,511,480 | B1 | 1/2003 | Tetzlaff et al. |
| 6,033,399 | A | 3/2000 | Gines | 6,514,251 | B1 | 2/2003 | Ni et al. |
| 6,039,733 | A | 3/2000 | Buysse et al. | 6,544,264 | B1 | 4/2003 | Levine et al. |
| 6,041,679 | A | 3/2000 | Slater et al. | 6,562,037 | B1 | 5/2003 | Paton et al. |
| 6,050,996 | A | 4/2000 | Schmaltz et al. | 6,569,162 | B1 | 5/2003 | He |
| 6,053,914 | A | 4/2000 | Eggers et al. | 6,585,735 | B1 | 7/2003 | Frazier et al. |
| 6,053,933 | A | 4/2000 | Balazs et al. | 6,620,161 | B1 | 9/2003 | Schulze et al. |
| D424,694 | S | 5/2000 | Tetzlaff et al. | 6,626,901 | B1 * | 9/2003 | Treat et al. .................. 606/29 |
| D425,201 | S | 5/2000 | Tetzlaff et al. | 6,652,521 | B1 | 11/2003 | Schulze |
| RE36,795 | E | 7/2000 | Rydell | 6,682,528 | B1 | 1/2004 | Frazier et al. |
| 6,083,223 | A | 7/2000 | Baker | 6,685,724 | B1 | 2/2004 | Haluck |
| 6,086,586 | A | 7/2000 | Hooven | 6,733,498 | B1 | 5/2004 | Paton et al. |
| 6,087,552 | A | 7/2000 | Gregory | 6,743,229 | B1 | 6/2004 | Buysse et al. |
| 6,090,107 | A | 7/2000 | Borgmeier et al. | D496,997 | S | 10/2004 | Dycus et al. |
| 6,096,031 | A | 8/2000 | Mitchell et al. | D499,181 | S | 11/2004 | Dycus et al. |
| 6,096,037 | A | 8/2000 | Mulier et al. | 6,926,716 | B1 | 8/2005 | Baker et al. |
| 6,099,550 | A | 8/2000 | Yoon | 6,929,644 | B1 | 8/2005 | Csaba et al. |
| 6,102,909 | A | 8/2000 | Chen et al. | 6,942,662 | B1 | 9/2005 | Goble et al. |
| 6,110,171 | A | 8/2000 | Rydell | 2002/0013583 | A1 | 1/2002 | Camran et al. |
| 6,110,212 | A | 8/2000 | Gregory | 2002/0099372 | A1 | 7/2002 | Schulze et al. |
| 6,113,596 | A | 9/2000 | Hooven et al. | 2002/0107517 | A1 | 8/2002 | Witt et al. |
| 6,113,598 | A | 9/2000 | Baker | 2002/0111624 | A1 | 8/2002 | Witt et al. |
| 6,117,158 | A | 9/2000 | Measamer et al. | 2002/0188294 | A1 | 12/2002 | Couture et al. |
| 6,123,701 | A | 9/2000 | Nezhat | 2003/0018331 | A1 | 1/2003 | Dycus et al. |

| | | | | | | |
|---|---|---|---|---|---|---|
| 2003/0069571 A1 | 4/2003 | Treat et al. | | EP | 1055400 A1 | 11/2000 |
| 2003/0078578 A1 | 4/2003 | Truckai et al. | | EP | 1080694 A1 | 3/2001 |
| 2003/0078597 A1* | 4/2003 | Blatter et al. ............... 606/139 | | EP | 1082944 A1 | 3/2001 |
| 2003/0139741 A1 | 7/2003 | Goble et al. | | EP | 1159926 A2 | 12/2001 |
| 2003/0139742 A1 | 7/2003 | Wampler et al. | | EP | 1330991 A1 | 7/2003 |
| 2003/0158549 A1 | 8/2003 | Swanson | | EP | 14861772 | 6/2004 |
| 2003/0199869 A1 | 10/2003 | Johnson et al. | | EP | 1532932 A1 | 5/2005 |
| 2003/0220637 A1 | 11/2003 | Truckai et al. | | GB | 2214430 A | 6/1989 |
| 2003/0236325 A1 | 12/2003 | Bonora | | JP | 501068 | 9/1984 |
| 2003/0236518 A1* | 12/2003 | Marchitto et al. ............ 606/27 | | JP | 502328 | 3/1992 |
| 2004/0049185 A1 | 3/2004 | Latterell et al. | | JP | 5-40112 | 2/1993 |
| 2004/0116979 A1 | 6/2004 | Truckai et al. | | JP | 06343644 A2 | 12/1994 |
| 2004/0147925 A1 | 7/2004 | Buysse et al. | | JP | 07265328 A2 | 10/1995 |
| 2004/0225288 A1 | 11/2004 | Buysse et al. | | JP | 08056955 A2 | 3/1996 |
| 2004/0230189 A1 | 11/2004 | Keppel | | JP | 08252263 A2 | 10/1996 |
| 2004/0236325 A1 | 11/2004 | Tetzlaff et al. | | JP | 09010223 A2 | 1/1997 |
| 2004/0243125 A1 | 12/2004 | Dycus et al. | | JP | 11244298 A2 | 9/1999 |
| 2004/0249371 A1 | 12/2004 | Dycus et al. | | JP | 200342599 A2 | 12/2000 |
| 2004/0249374 A1 | 12/2004 | Tetzlaff et al. | | JP | 200350732 A2 | 12/2000 |
| 2004/0250419 A1 | 12/2004 | Sremcich et al. | | JP | 2000342599 A2 | 12/2000 |
| 2004/0254573 A1 | 12/2004 | Dycus et al. | | JP | 2000350732 A2 | 12/2000 |
| 2005/0004564 A1 | 1/2005 | Wham et al. | | JP | 2001008944 A2 | 1/2001 |
| 2005/0004568 A1 | 1/2005 | Lawes et al. | | JP | 2001029356 A2 | 2/2001 |
| 2005/0004570 A1 | 1/2005 | Chapman et al. | | JP | 2001128990 A2 | 5/2001 |
| 2005/0021025 A1 | 1/2005 | Buysse et al. | | SU | 401367 | 11/1974 |
| 2005/0021026 A1 | 1/2005 | Baily | | WO | WO 92/06642 | 4/1992 |
| 2005/0021027 A1 | 1/2005 | Shields et al. | | WO | WO 94/08524 A | 4/1994 |
| 2005/0033278 A1 | 2/2005 | McClurken et al. | | WO | WO 95/02369 | 1/1995 |
| 2005/0101951 A1 | 5/2005 | Wham et al. | | WO | WO 95/07662 | 3/1995 |
| 2005/0101952 A1 | 5/2005 | Lands et al. | | WO | WO 96/022056 | 7/1996 |
| 2005/0107784 A1 | 5/2005 | Moses et al. | | WO | WO 96/13218 | 9/1996 |
| 2005/0107785 A1 | 5/2005 | Dycus et al. | | WO | WO 97/00647 | 1/1997 |
| 2005/0113818 A1 | 5/2005 | Sartor et al. | | WO | WO 97/00648 | 1/1997 |
| 2005/0113819 A1 | 5/2005 | Wham et al. | | WO | WO 97/10764 | 3/1997 |
| 2005/0113826 A1 | 5/2005 | Johnson et al. | | WO | WO 97/24073 | 7/1997 |
| 2005/0113827 A1 | 5/2005 | Dumbauld et al. | | WO | WO 97/24993 | 7/1997 |
| 2005/0113828 A1 | 5/2005 | Shields et al. | | WO | WO 98/27880 | 7/1998 |
| 2005/0119655 A1 | 6/2005 | Moses et al. | | WO | WO 99/03407 | 1/1999 |
| 2005/0149151 A1 | 7/2005 | Orszulak et al. | | WO | WO 99/03408 | 1/1999 |
| 2006/0079891 A1 | 4/2006 | Arts et al. | | WO | WO 99/03409 | 1/1999 |
| | | | | WO | WO 99/12488 A | 3/1999 |
| | FOREIGN PATENT DOCUMENTS | | | WO | WO 99/40857 | 8/1999 |
| DE | 2415263 | 10/1975 | | WO | WO 99/040861 | 8/1999 |
| DE | 8712328 | 3/1988 | | WO | WO 99/51158 | 10/1999 |
| DE | 29616210 | 1/1997 | | WO | WO 99/066850 | 12/1999 |
| DE | 19608716 | 4/1997 | | WO | WO 99/66850 A | 12/1999 |
| DE | 19751108 | 5/1999 | | WO | WO 00/24330 | 5/2000 |
| EP | 0364216 A1 | 4/1990 | | WO | WO 00/24331 | 5/2000 |
| EP | 518230 A1 | 12/1992 | | WO | WO 00/41638 | 7/2000 |
| EP | 0 541 930 B1 | 5/1993 | | WO | WO 00/53112 | 9/2000 |
| EP | 0572131 | 12/1993 | | WO | WO 01/17448 A | 3/2001 |
| EP | 584787 A1 | 3/1994 | | WO | WO 01/54604 | 8/2001 |
| EP | 0623316 A1 | 11/1994 | | WO | WO 02/07627 | 1/2002 |
| EP | 0624348 A2 | 11/1994 | | WO | WO 02/080783 | 10/2002 |
| EP | 0650701 A1 | 5/1995 | | WO | WO 02/080784 | 10/2002 |
| EP | 0694290 A3 | 3/1996 | | WO | WO 02/080785 | 10/2002 |
| EP | 0717966 A1 | 6/1996 | | WO | WO 02/080786 | 10/2002 |
| EP | 0754437 A3 | 3/1997 | | WO | WO 02/080793 | 10/2002 |
| EP | 853922 A1 | 7/1998 | | WO | WO 02/080794 | 10/2002 |
| EP | 0875209 A1 | 11/1998 | | WO | WO 02/080795 | 10/2002 |
| EP | 0878169 A1 | 11/1998 | | WO | WO 02/080796 | 10/2002 |
| EP | 0887046 A3 | 1/1999 | | WO | WO 02/080796 A1 | 10/2002 |
| EP | 0923907 A1 | 6/1999 | | WO | WO 02/080797 | 10/2002 |
| EP | 0986990 A1 | 3/2000 | | WO | WO 02/080798 | 10/2002 |
| EP | 1034747 A1 | 9/2000 | | WO | WO 02/080799 | 10/2002 |
| EP | 1034748 A1 | 9/2000 | | WO | WO 02/081170 | 10/2002 |
| EP | 1025807 A3 | 10/2000 | | WO | WO 03/101311 | 12/2003 |
| EP | 1034746 A3 | 10/2000 | | WO | WO 04/032777 | 4/2004 |
| EP | 1050278 A1 | 11/2000 | | WO | WO 2004/052221 A1 | 6/2004 |
| EP | 1053719 A1 | 11/2000 | | WO | WO 04/073490 | 9/2004 |
| EP | 1053720 A1 | 11/2000 | | WO | WO 04/082495 | 9/2004 |
| EP | 1055399 A1 | 11/2000 | | WO | WO 2004/082495 A1 | 9/2004 |
| | | | | WO | WO 2004/098383 A1 | 11/2004 |

WO  WO 04/103156  12/2004

OTHER PUBLICATIONS

PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clincal trial of Ligasure versus open haemorrhoidectomy" British Journal of Surgery 2002, 89, 154-157.
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, ☐Apr. 2001 pp. 236-237.

W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, ☐Jun. 2003.
Craig Johnson, "Use of the LigaSure Vessel Sealing System in Bloodless Hemorrhoidectomy" Innovations That Work, ☐Mar. 2000.
Muller et al., "Extended Left Hemicolectomy Using the LigaSure Vessel Sealing System" Innovations That Work, ☐Sep. 1999.
Herman et al., "Laparoscopic Intestinal Resection With the LigaSure Vessel Sealing System: A Case Report" Innovations That Work, ☐Feb. 2002.
Carus et al., "Initial Experience With The LigaSure Vessel Sealing System in Abdominal Surgery" Innovations That Work,☐Jun. 2002.
Levy et al. "Randomized Trial of Suture Versus Electrosurgical Bipolar Vessel Sealing in Vaginal Hysterectomy"Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3.
E. David Crawford "Use of a Novel Vessel Sealing Technology in Management of the Dorsal Veinous Complex" Sales/Product Literature.
Jarrett et al., "Use of the LigaSure Vessel Sealing System for Peri-Hilar Vessels in Laparoscopic Nephrectomy" Sales/Product Literature.
E. David Crawford "Evaluation of a New Vessel Sealing Device in Urologic Cancer Surgery" Sales/Product Literature.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature.
Johnson et al. "Evaluation of a Bipolar electrothermal Vessel Sealing Device in Hemorrhoidectomy" Sales/Product Literature.
Int'l Search Report PCT/US01/11218.
Int'l Search Report PCT/US99/24869.
Int'l Search Report PCT/US98/18640.
Int'l Search Report PCT/US98/23950.
Int'l Search Report EP 05013463.4, dated Sep. 28, 2005.
Int'l Search Report EP 0501913.3, dated Oct. 18, 2005.
Int'l Search Report EP 05020665.5, dated Feb. 16, 2006.
Int'l Search Report EP 05020666.3, dated Feb. 17, 2006.
Int'l Search Report EP 05021779.3, dated Jan. 18, 2006.
Int'l Search Report EP 05021197.8, dated Jan. 31, 2006.
Int'l Search Report EP 05021937.7, dated Jan. 13, 2006.
Int'l Search Report—extended- EP 05021937.7, dated Mar. 6, 2006.
Int'l Search Report EP 05023017.6, dated Feb. 16, 2006.
Int'l Search Report EP 05021780.1, dated Feb. 9, 2006.
Int'l Search Report EP 06002279.5, dated Mar. 22, 2006.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Technique in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.

Johnson et al. "Evaluation of a Bipolar electrothermal Vessel Sealing Device in Hemorrhoidectomy" Sales Product Literature; Jan. 2004.

La Joie et al. "Welding Artificial Biomaterial with a Pulsed Diode Laser and Indocyanine Green Dye" Lasers in Surgery, Advanced Characterization, Therapeutics, and Systems, V.R.R. Anderson Ed. Proc SPIE 508-516 (1995).

International Search Report PCT/US01/11224, dated Nov. 13, 2001.

International Search Report EP 98958575.7, dated Sep. 20, 2002.

International Search Report EP 04013772, dated Apr. 1, 2005.

International Search Report EP 05013895, dated Oct. 14, 2005.

International Search Report EP 05017281, dated Nov. 16, 2005.

US 6,663,629, 12/2003, Buysse et al. (withdrawn)

* cited by examiner

Normal Aorta

NaOH/Boiled Aorta

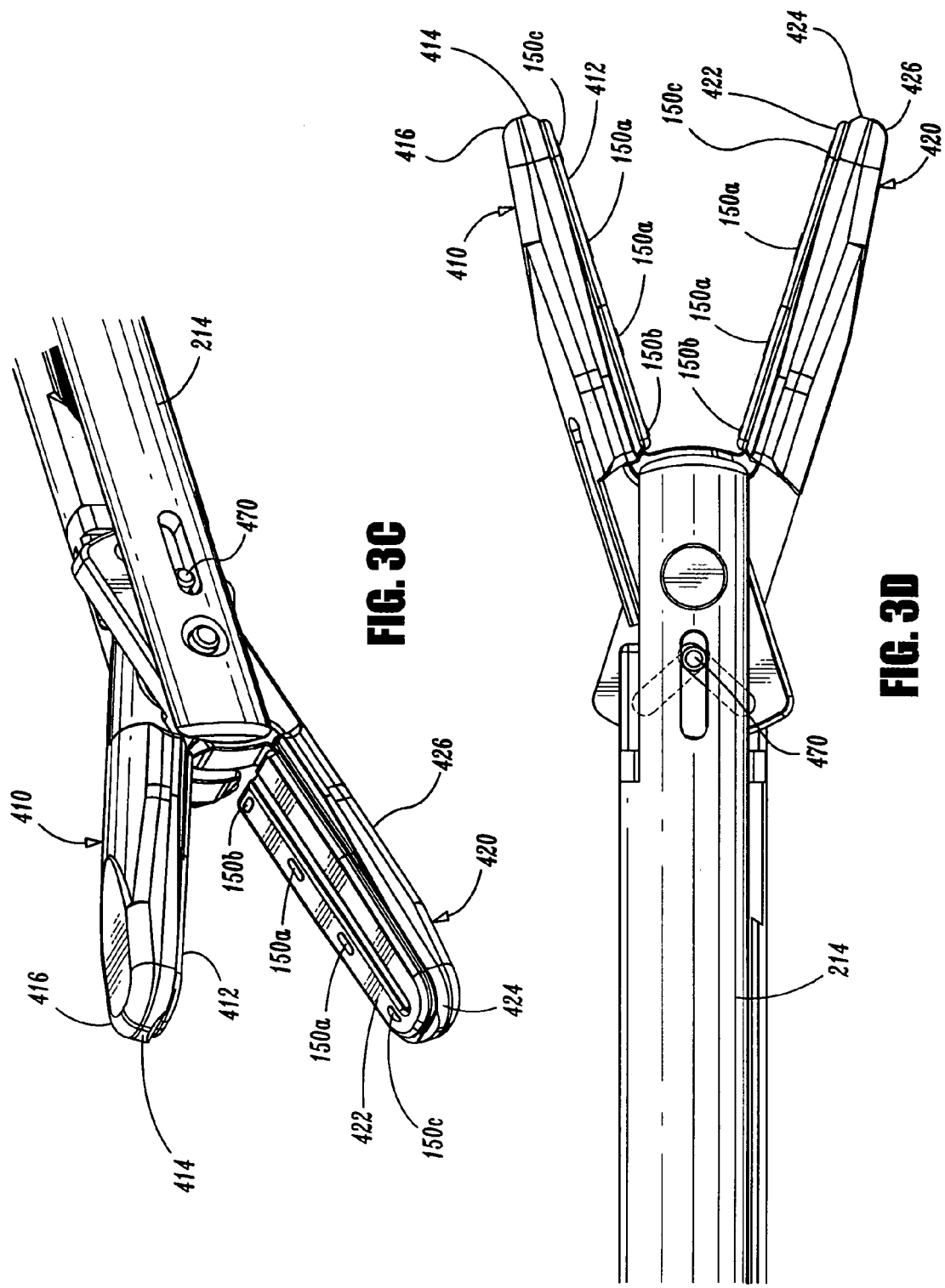

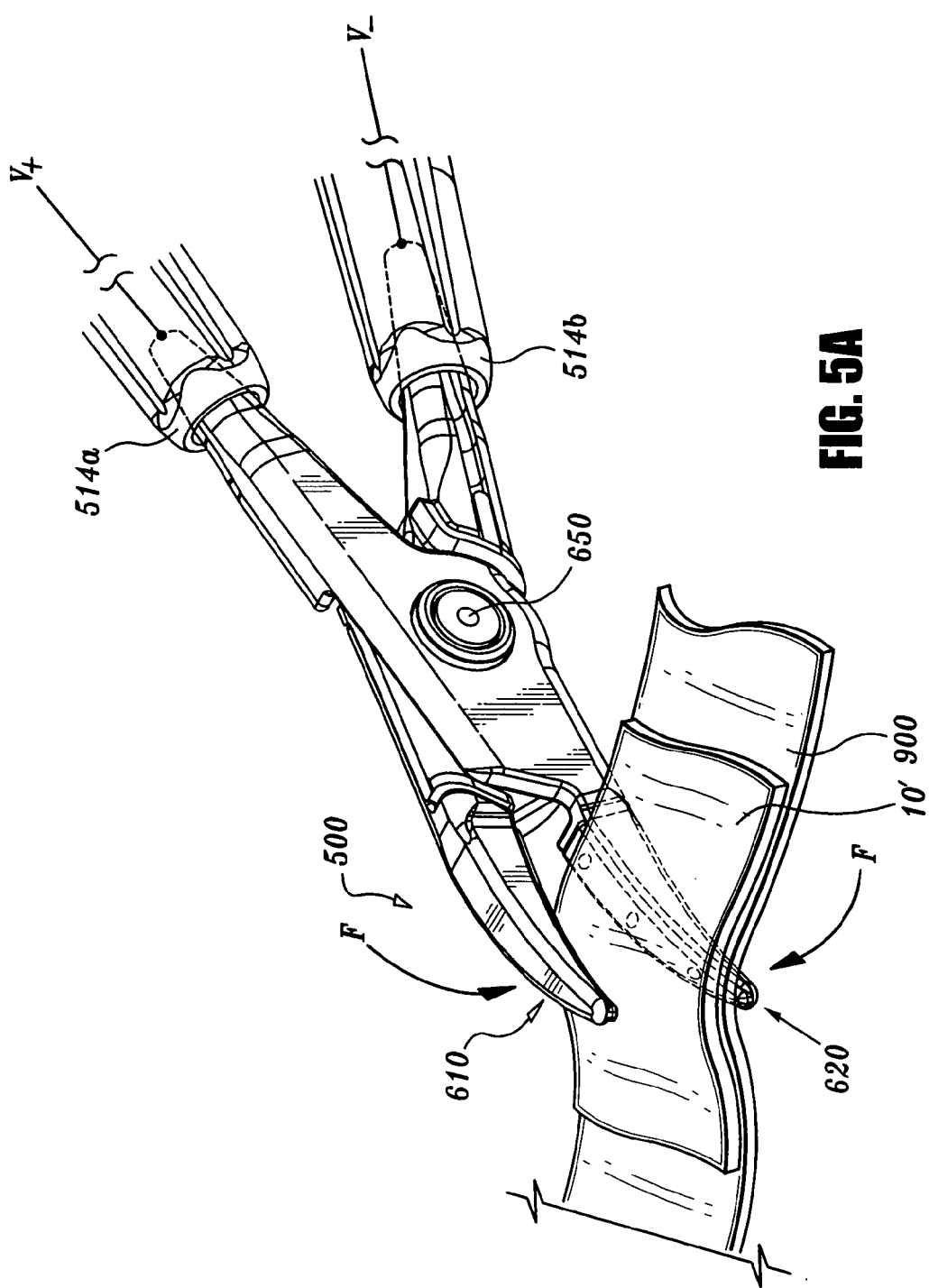

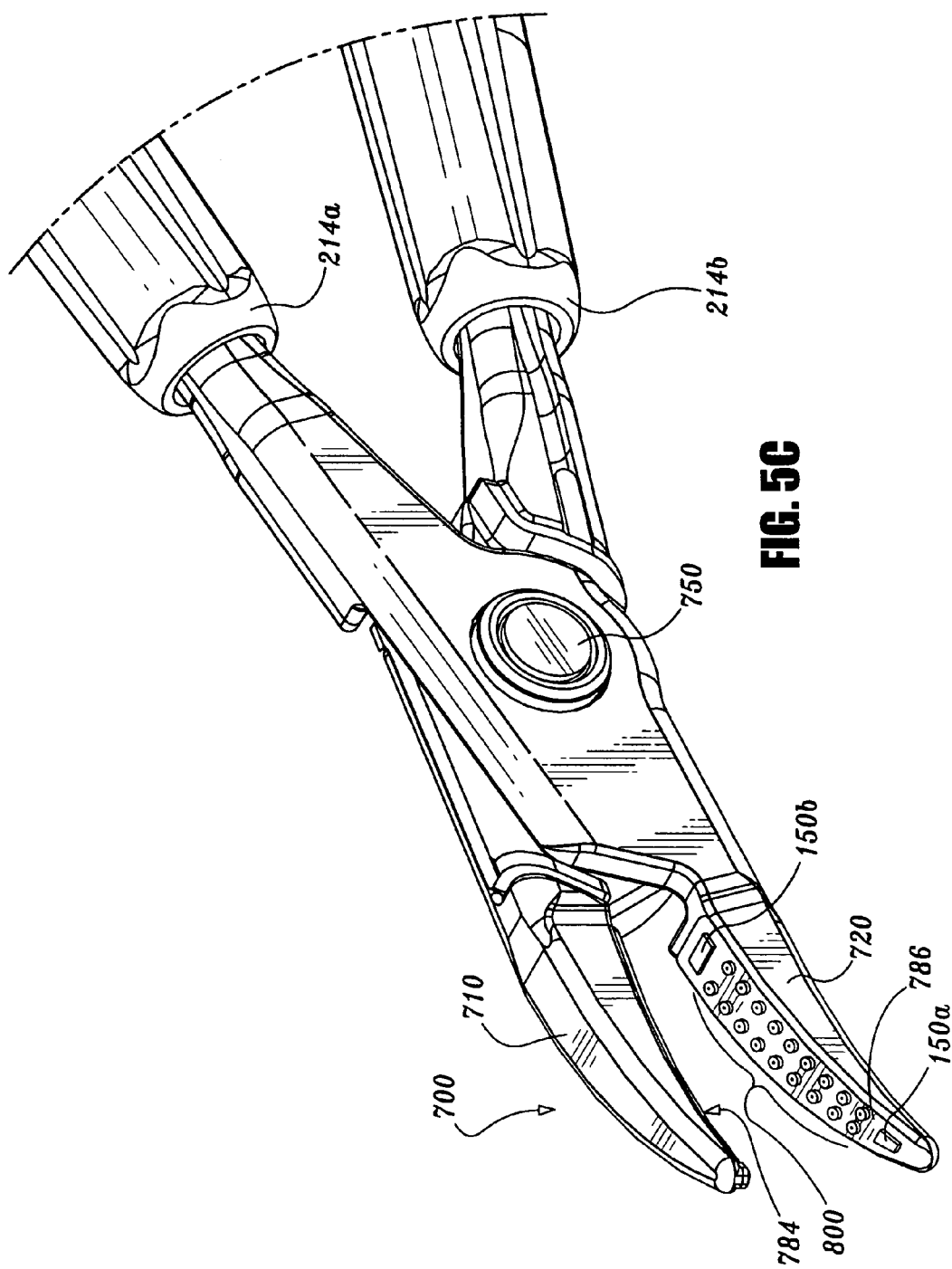

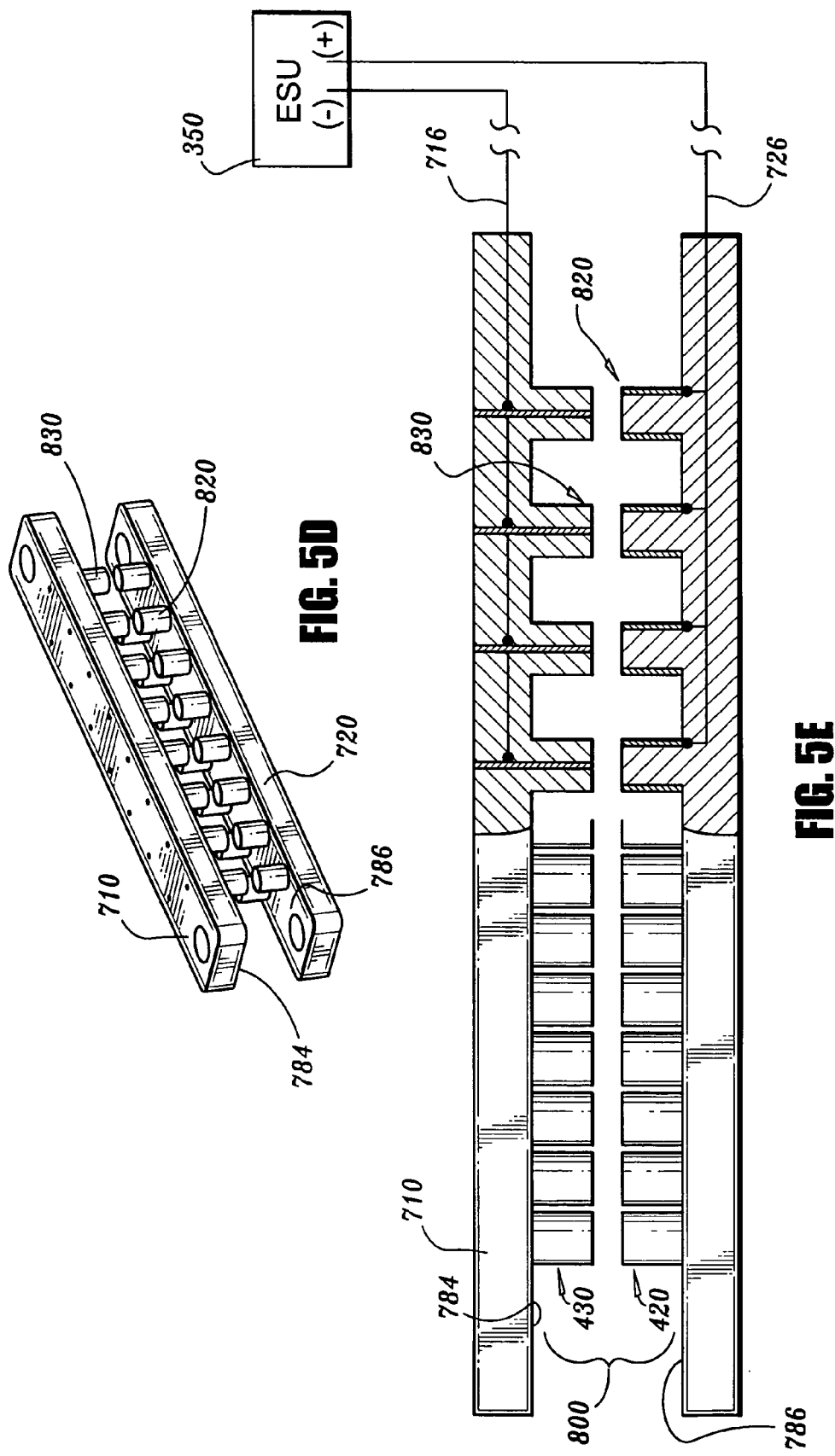

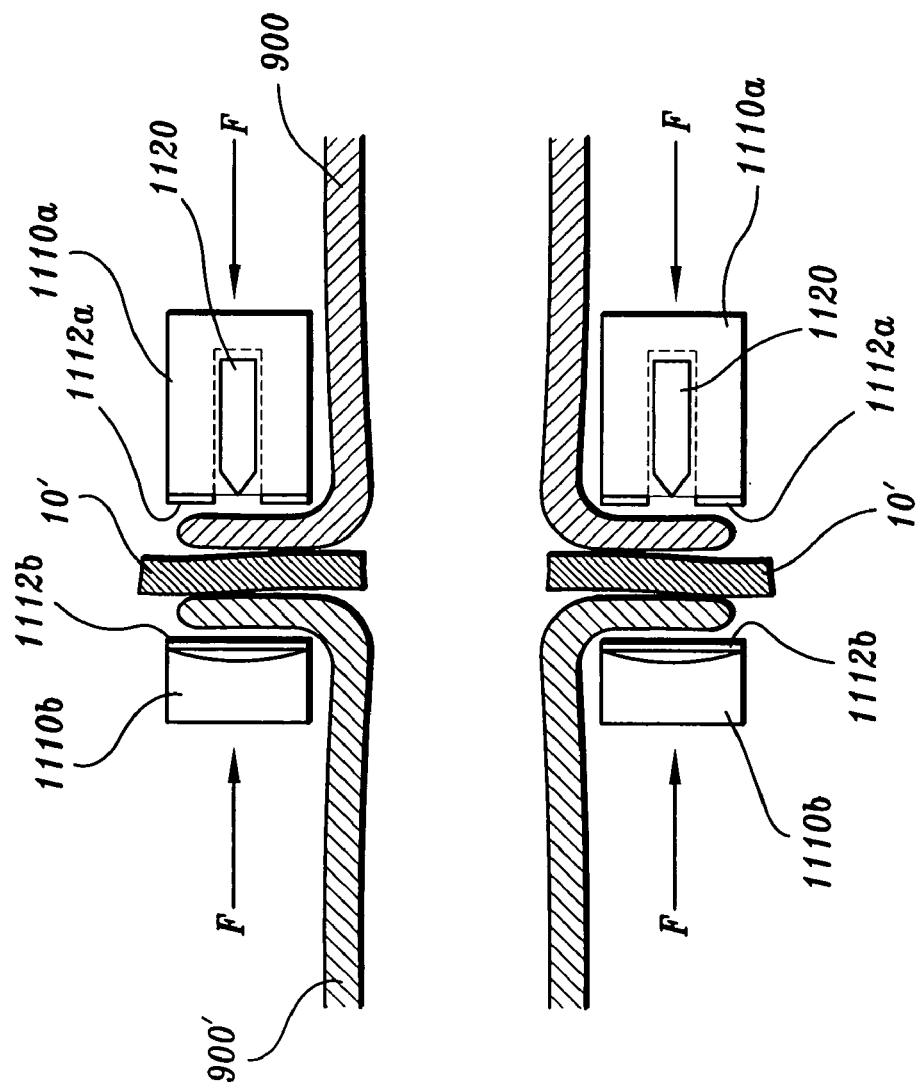

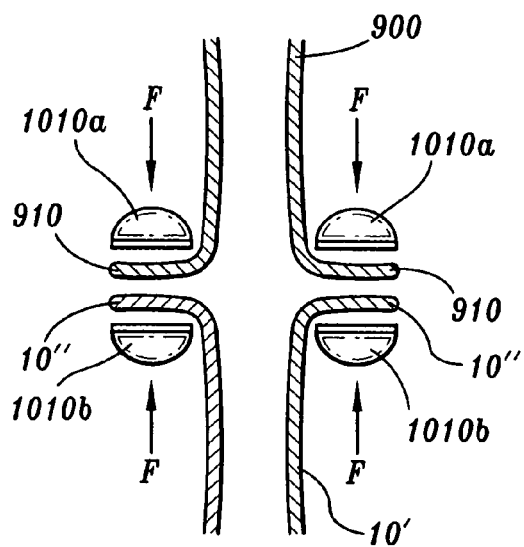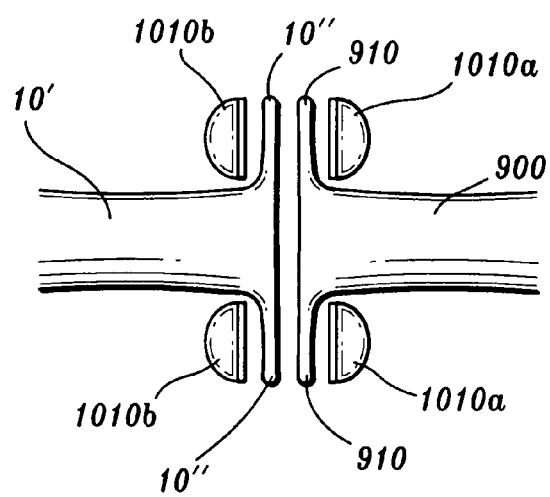
FIG. 9A
FIG. 9B
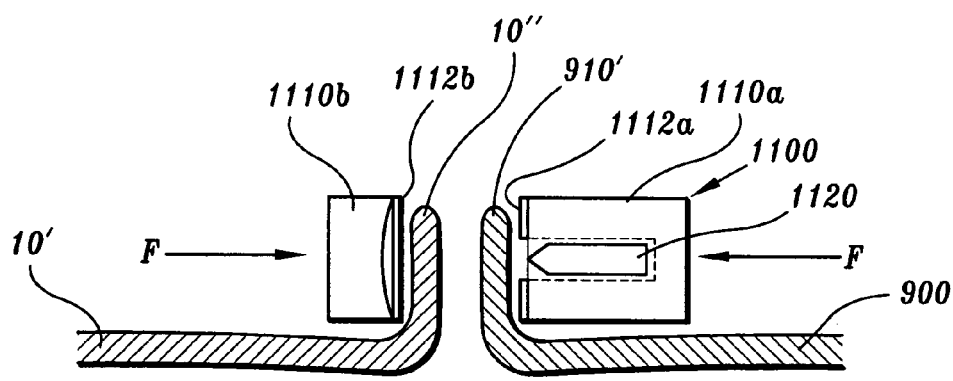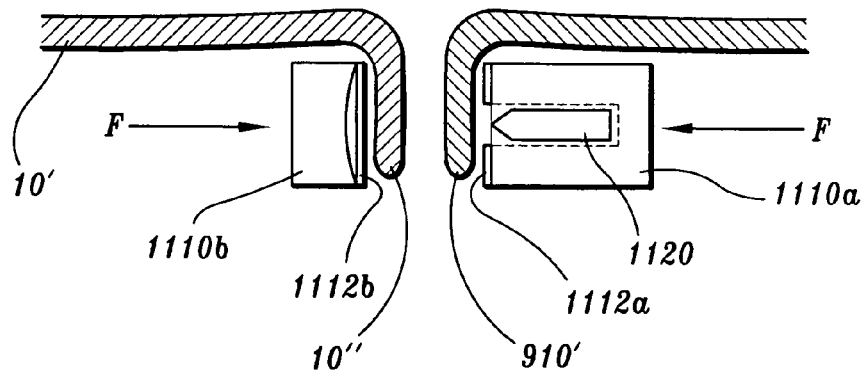
FIG. 10

METHOD OF FUSING BIOMATERIALS WITH RADIOFREQUENCY ENERGY

CROSS REFERENCE TO RELATED APPLICATION

The present application claims the benefit of priority to U.S. Provisional Application Ser. No. 60/467,181 filed on May 1, 2003 by Ali Bailey, the entire contents of which being incorporated by reference herein.

BACKGROUND

The present disclosure relates to a method of fusing biomaterial utilizing RF energy and, more particularly, the present disclosure relates to a method of fusing biomaterials to tissue or other biomaterials utilizing vessel or tissue sealing technology employing a unique combination of RF energy, pressure and gap distance to effectively seal or fuse tissue.

TECHNICAL FIELD

During a large majority of operations, surgeons typically utilize sutures, clips and/or some other type of surgical fastener to hold adjacent tissue in opposition to promote tissue healing, graft two (or more) tissues together and/or perform an anastomosis between two tissue structures. In certain instances, biodegradable sutures are used, e.g., collagen "gut" sutures or synthetic polymer sutures, which have the added benefit of integrating with the body over time or dissolving thus eliminating many adverse reactions to the suture or "foreign body".

In some instances, additional materials such as biomaterial patches may be used in conjunction with the sutures and/or staples to provide additional strength during the initial amalgamation of the tissue and/or during the pendancy of the tissue repair. For example, polypropylene mesh patches have been used in connection with hernia tissue repair and hernia reconstruction. The patches may also be made from two layers of superimposed collagen, one layer being a porous adhesive layer of fibrous collagen sponge and the other layer being a dense collagen and/or gelatin film.

Biological glues utilizing fibrin polymerization have also been used to provide a nontoxic, flowable material which sets into a solid to join tissue. However, these glues tend to have low adhesive strength and are more suitable for use as biological sealants which work in conjunction with other mechanical securement means, staples, sutures, etc. to join tissue.

Other techniques for tissue repair and tissue anastomosis have also been developed such as laser welding where a laser, e.g., ND:YAG, CO2, etc., applies light energy to thermally heat the tissue to a point where the tissue proteins denature and the collagenous elements of the tissue form a "biological glue" which adheres the tissue after the tissue area cools. However, the weakness of the weld joint is a primary disadvantage of laser welding, and various filler materials such as collagen must be introduced to improve the strength of the weld joint.

Elastic fibers have also been proposed for use with laser welding. Elastic fibers are responsible for the elastic properties of several tissues such as skin, lung and blood vessels, and are partially composed of elastin in a microfibril arrangement. Microfibrils make up the overall fiber structure and assembly and are responsible for the rubber-like elasticity of the fibers. Again, elastin is found in many tissue types, e.g., skin, blood vessels, lung tissue, etc. and imparts strength and flexibility to those tissues. Elastin may be employed as a support structure to sustain a section of body tissue such as a vascular stent, a vascular conduit, a ureter replacement, or as a stent or conduit covering, coating or lining. It can also be utilized to provide a graft suitable for use in repairing a lumen wall in various tissue replacement procedures, or for stomach, lung, or heart repair. Elastin may also be used in colon repair or replacement, for skin repair or replacement, and/or as a cosmetic implantation or breast implant.

U.S. Pat. Nos. 5,989,244, 5,990,379, 6,087,552, 6,110, 212 and 6,372,228, discuss the utilization of elastin and elastin-based materials to repair tissue structures, support body tissue and/or graft tissue structures by laser welding. More particularly, the techniques described in these patents disclose the utilization of laser energy in combination with photosensitizing or energy absorbing dyes, e.g., indocyanine green dye, to thermally bond elastin-based materials to a tissue sight. The energy absorbing dye is applied to the tissue site and/or the elastin material. Because the dye has an absorption peak at a wavelength corresponding to the wavelength emitted by the laser, the tissue and the elastin-based material absorb much less light at the same wavelength and the energy and resulting thermal effects are generally confined to a predefined zone around the dye. Ideally, the absorbance of the dye layer is previously or concurrently determined so that the optimal amount of light for optimal bonding can be delivered.

As mentioned in these aforementioned patents, laser welding is a process whose success is dependent upon the proper management and control of many key properties which ultimately effect the overall success of fusing elastin-based materials and tissue substrates. Some of these key properties include: the magnitude of the wavelength, energy level, absorption rate, and light intensity during irradiation and the concentration of the energy absorbing material.

Unfortunately, laser welding is a relatively complex process which relies heavily on the use of energy-absorbing dyes with varying wavelengths and large and expensive laser units to thermally fuse the elastin-based materials and the tissue substrates. It would therefore be desirable to provide a simpler and less expensive method and process for fusing biomaterials to tissue substrates or other biomaterials without relying on energy absorbing dyes or expensive laser units.

Vessel sealing or tissue sealing is a recently-developed technology which utilizes a unique combination of radiofrequency energy, pressure and gap control to effectively seal or fuse tissue between two opposing jaw members or sealing plates. Vessel or tissue sealing is more than "cauterization" which is defined as the use of heat to destroy tissue (also called "diathermy" or "electrodiathermy") and vessel sealing is more than "coagulation" which is defined as a process of desiccating tissue wherein the tissue cells are ruptured and dried. "Vessel sealing" is defined as the process of liquefying the collagen, elastin and ground substances in the tissue so that it reforms into a fused mass with significantly-reduced demarcation between the opposing tissue structures.

In order to effectively "seal" tissue or vessels, two predominant mechanical parameters must be accurately controlled: 1) the pressure applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that a good seal for certain tissues is optimum between 0.001 inches and 0.006 inches. For other tissues and biomaterials, other ranges may apply for optimum sealing. In any instance it is important to determine seal ranges for particular tissue types since below certain ranges, seals may shred or tear and above certain ranges the tissue may not be properly or effectively sealed.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Thus, a need exists to develop a relatively simple and inexpensive method of fusing elastin or elastin-based biomaterials to tissue substrates and/or other elastin-based biomaterials utilizing the benefits of vessel sealing technology and without utilizing energy absorbing dyes or large expensive laser units.

SUMMARY

The present disclosure relates to a method of fusing biomaterial and tissue using radiofrequency energy and includes the steps of: providing a vessel sealing instrument having opposing jaw members which are movable relative to one another to compress tissue therebetween. The vessel sealing instrument includes at least one stop member affixed thereto for regulating the distance between opposing jaw members. Preferably, the stop member(s) project from an electrically conductive sealing surface of each opposing jaw member to regulate the distance to within a range of about 0.004 inches to about 0.010 inches.

The method also includes the steps of: providing a biomaterial (e.g., elastin biomaterial, collagen-based biomaterials, elastin-based biomaterials and fibrin-based biomaterials); positioning the biomaterial in abutting relation to tissue; approximating the biomaterial and tissue between the jaw members; compressing the biomaterial and tissue between the jaw members under a working pressure preferably within the range of about 3 kg/cm$^2$ to about 16 kg/cm$^2$; and energizing the jaw members with radiofrequency energy to effectively fuse the biomaterial and the tissue such that the biomaterial and the tissue reform into a single, fused mass. The method may also include the steps of: extracting collagen from the biomaterial; and confirming the absence of collagen from the biomaterial.

Preferably, the stop member(s) of the providing step regulates the distance between opposing jaw members within the range of about 0.004 inches to about 0.010 inches for larger tissue structure with elastin and about 0.001 inches to about 0.006 inches for smaller tissue structures with elastin. In one embodiment, the biomaterial is shaped, e.g., tubular, for performing an anastomosis. In other embodiments, the biomaterial is shaped in a patch for tissue repair or tissue replacement.

Another method of fusing biomaterial and tissue using radiofrequency energy according to the present disclosure includes the steps of: providing a circular stapling instrument having a stapler support member which supports an array of staples and an opposing anvil. The support member is movable relative to the anvil to compress tissue therebetween. Preferably, the stapler support member and the anvil include electrically conductive sealing surfaces.

The method also includes the steps of: everting an end of a segment of biomaterial; positioning the everted end of the biomaterial in abutting relation to an everted tissue end such that the respective intimae of the everted biomaterial and the tissue oppose one another; compressing the biomaterial and tissue between the stapler support member and the anvil under a working pressure within the range of about 3 kg/cm$^2$ to about 16 kg/cm$^2$ (and, preferably within the working range of about 4.5 kg/cm$^2$ to about 8.5 kg/cm$^2$) between energizing the support member and the anvil with radiofrequency energy to effectively fuse the biomaterial and the tissue such that the tissue and the biomaterial reform into a single, fused mass; and actuating the circular stapling instrument to fire the staples through the biomaterial and tissue and against the anvil.

Yet another method of fusing biomaterial and tissue using radiofrequency energy according to the present disclosure includes the steps of: providing a circular stapling instrument similar to the one described above and providing a biomaterial. The method also includes the steps of: everting the ends of two tissue segments to expose tissue intimae; positioning at least one segment of biomaterial between the everted ends of the two tissue segments; compressing the two tissue segments and the biomaterial between the stapler support member and the anvil under a working pressure; energizing the support member and the anvil with radiofrequency energy to effectively fuse the biomaterial and the two tissue segments such that the two tissue segments and the biomaterial reform into a single, fused mass; and actuating the circular stapling instrument to deform the staple through the biomaterial and tissue and against the anvil.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Various embodiments of the subject methods and component parts associated therewith are described herein with reference to the drawings wherein:

FIG. 3C is an enlarged, side, perspective view of an end effector of the forceps of FIG. 3A;

FIG. 3D is an enlarged, side view of the end effector of FIG. 3C;

FIG. 5A is an enlarged, side, perspective view of the forceps of FIG. 4A shown approximating tissue and biomaterial between two opposing jaw members;

FIG. 5C is an enlarged, side, perspective view of an alternate electrode assembly for use with sealing biomaterials;

FIGS. 5D and 5E are schematic representations of the electrode assembly of FIG. 5C.

FIG. 8 is a schematic representation of one gasket-shaped biomaterial being fused between everted tissue ends to enhance an end-to-end anastomosis with an anastomotic stapler;

FIGS. 9A and 9B are schematic representations of a biomaterial and tissue being directly fused between two opposing jaw members to perform an end-to-end anastomosis; and FIG. 10 is a schematic representation of a biomaterial being fused directly with everted tissue to enhance an end-to-end anastomosis with an anastomotic stapler.

DETAILED DESCRIPTION

Figure 1A:
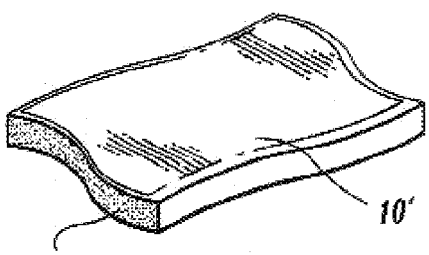
FIG. 1A is a perspective view of an elastin biomaterial according to the present disclosure which can be used with a radiofrequency vessel sealing instrument to repair, heal and/or replace tissue.

The present invention relates to biomaterials and to methods of fusing biomaterials to tissue (or other biomaterials) using so-called "vessel sealing" technology which involves a unique combination of radiofrequency (RF) energy, specified pressures and specific gap distances between opposing electrically conductive surfaces to effectively and consistently melt the tissue and/or biomaterial into a fused mass with limited demarcation. For the purposes herein, the term "biomaterials" includes collagen-based materials, elastin-based materials and fibrin-based materials and elastin. The biomaterials may be natural, synthetic and/or engineered biomaterials depending upon a particular purpose.

It is envisioned that the biomaterials may be sealed or fused to tissue substrates, soft tissue (lung, intestine, bowel, blood vessels, muscles, skin, etc.) or other biomaterials utilizing vessel sealing technology as a means for tissue healing, reconstruction, repair and/or replacement.

For the purposes herein, an elastin biomaterial will be discussed, however, it is envisioned that other biomaterials may also be utilized in a similar fashion to accomplish the same or similar purposes as described herein. For example, there are many types of collagen biomaterial sheets, collagenous bioartificial blood vessels, and collagen grafts. Various methods exist for the manufacture of different biomaterials. Moreover, collagen can come from naturally occurring tissues such as dura matter or pericardium, or the collagen may be reconstituted into collagen sheets made from either bovine intestines, bovine skin, or Achilles tendon which are bathed in or combined with proteolytic enzymes, acids, alkalis, and/or ethylene oxides. Spidroin, the elastin-like protein in spider webs, may also be used as a biomaterial for the purposes herein.

Elastin biomaterials are advantageous in certain types of tissue repair. Many known techniques are available for preparing elastin biomaterials such as those techniques described in U.S. Pat. Nos. 4,132,746, 4,500,700, 4,187,852, 4,589,882, 4,693,718, 4,783,523, 4,870,055, 5,064,430, 5,336,256 5,989,244, 5,990,379, 6,087,552, 6,110,212 and 6,372,228, the entire contents of all of which are hereby incorporated by reference herein.

For the purposes herein, one method of elastin lamina extraction is generally outlined below and is described by H. Shangguam et al. in the article entitled: "Pressure Effects on Soft Tissues Monitored by Changes in Tissue Optical Properties", *Laser-Tissue Interaction* IX, S. L. Jacques Ed., Proc. SPIE 3254, 366–371 (1998). To change a normal aorta into elastin lamina "biomaterial", the following steps may be taken:

Aortas are placed into 60° C. 0.5M NaOH for 1–1.5 hours to digest collagen and all tissue constituents except the elastin lamina;

The remaining elastin lamina is put into room-temperature deionized water for 30 minutes.

The remaining elastin lamina is put into boiling deionized water for 30 minutes to remove NaOH and sterilize the biomaterial; and The elastin biomaterial is kept in the saline and refrigerated.

To confirm the absence of collagen within the elastin biomaterial, special histological stains that target certain receptors on the collagen may be employed. Birefringence can also be used to check for collagen presence (collagen has a gold hue under birefringence light).

Any method of extracting/removing cellular material, proteins and fats from the tissue while leaving the extracellular elastin matrix intact can be used. For example, the methods can involve combinations of acidic, basic, detergent, enzymatic, thermal or erosive means, as well as the use of organic solvents. Alternatively, the tissue may be incubated or bathed in various solutions including: formic acid, trypsin, guanidine, ethanol, diethylether, acetone, t-butanol, and sonication. As can be appreciated, the incubation temperature and incubation time will vary depending on the starting material and extracting solution utilized. As explained in more detail below, the resulting elastin biomaterial may be molded so as to render it a suitable size and shape for any many different purposes. It is envisioned that fusing various biomaterials (e.g., collagen-to-elastin, collagen-to-tissue, elastin-to-elastin, elastin-to-tissue or collagen-to-collagen) will yield unique bonding characteristics (strength of seal, seal thickness, seal quality, seal consistency, etc.).

Figure 1B:
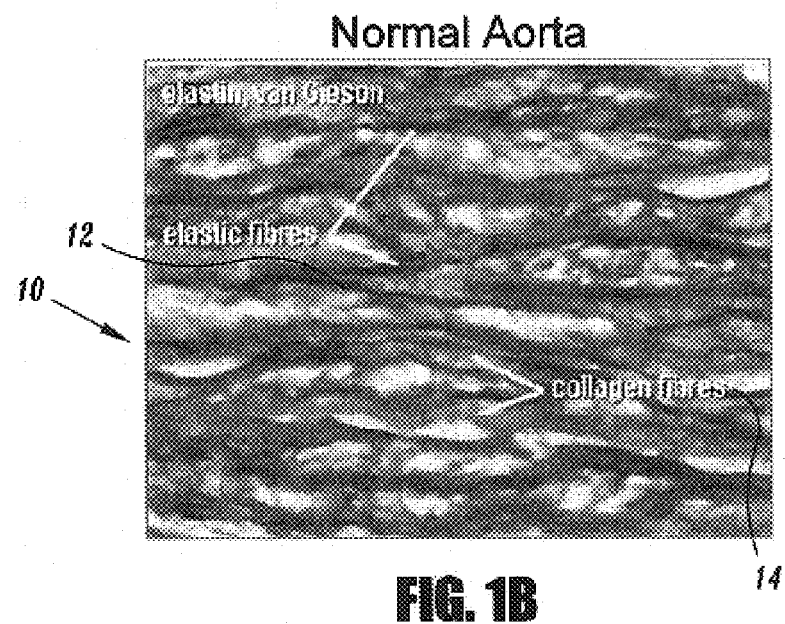
FIG. 1B is an enlarged microscopic view of a normal aorta showing both collagen and elastin fibers.
Figure 1C:
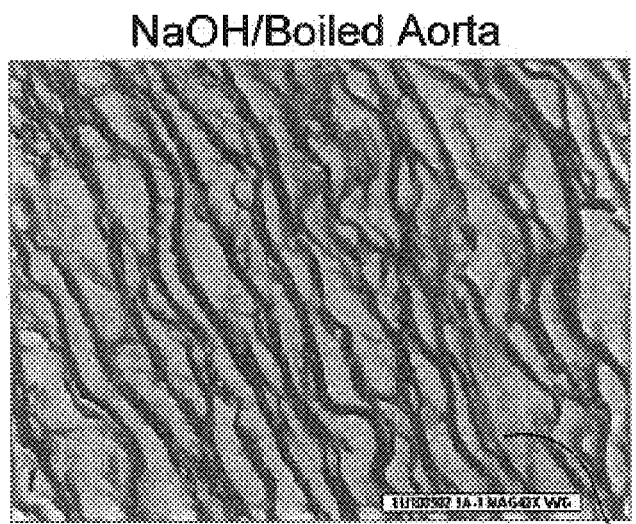
FIG. 1C is an enlarged, microscopic view (shown at 40× magnification) of an aorta which has been treated using a sodium hydroxide (NaOH) extraction process ("NaOH/Boiled")

FIGS. 1A and 1C show a schematic representation of a piece of elastin biomaterial (NaOH/Boiled aorta) 10' which has been prepared according to the above extraction process. The collagen 14 fibers have been eliminated from the material such that only elastin 12 remains. FIGS. 1B and 1C show before and after microscopic views (under a 40× magnification) of a normal aorta 10 prepared according to the above-identified extraction process. More particularly, FIG. 1B depicts a normal aorta 10 with both collagen 14 and elastin fibers 12 clearly evident. It is important to note the various histological stains which help distinguish the various fibers. Verhoeff's Van Geistan histological stain stains elastin fibers black (See FIG. 1C). Hematoxylin and Eosin (H&E) histological stain stains tissue pink (See FIG. 1B).

Figure 1D:
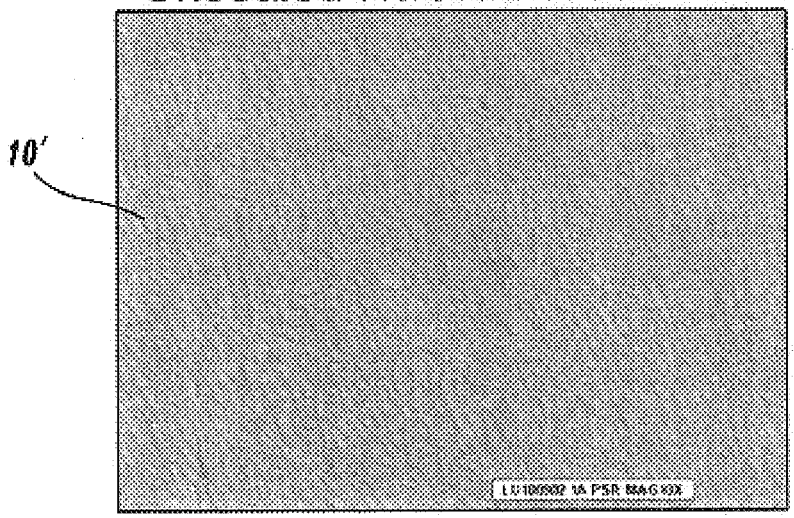
FIG. 1D is an enlarged, unfiltered microscopic view (shown at 10× magnification) of the unsealed NaOH/Boiled aorta of FIG. 1C.
Figure 1E:
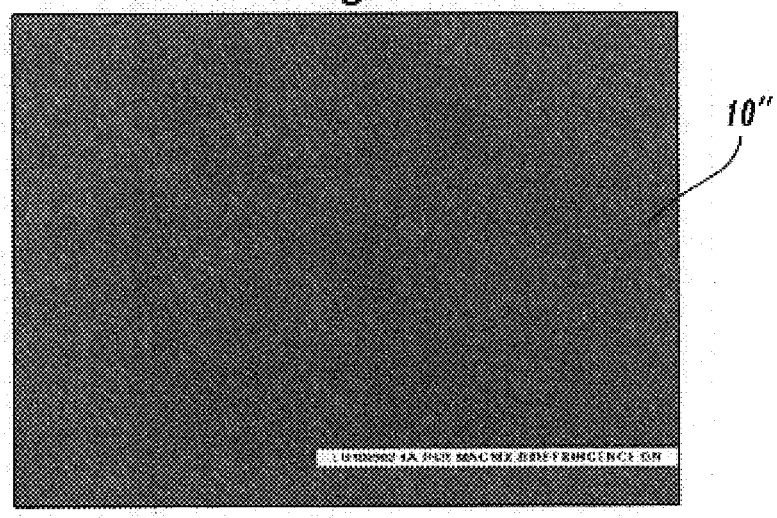
FIG. 1E is an enlarged, filtered microscopic view (shown at 10× magnification with a birefringence filter) of the unsealed NaOH/Boiled aorta of FIG. 1C confirming the absence of collagen from the biomaterial.

FIG. 1C shows the aorta 10' after being bathed in a 60° C. sodium hydroxide solution for approximately 1 to 1.5 hours to extract the collagen 14. FIG. 1D shows the aorta 10' at 10× magnification without the use of a birefringence filter. FIG. 1E shows the same aorta 10' at the same magnification under a birefringence filter, confirming the absence of the collagen fibers as a result of the extraction process (under a birefringence filter, collagen would birefringe in a gold-ish hue).

As can be appreciated, sheets or patches of elastin biomaterial 10' may be selectively varied in size, thickness and shape and/or may be formed into molds and scaffolding depending upon the intended purpose for the biomaterial. Specifically, the tubular nature of the normal aorta may be maintained if desired. Elastin biomaterial 10' may also be molded into tubular segments by injecting the elastin into tubular molds. Tubular segments may be made in virtually any size or length and the inner and outer tube diameter may vary according to a particular purpose. For example, a small tube may be used for a coronary arterial stent and a large tube of 1–5 inches in diameter may be used as an annularly welded patch for anastomosis of the small intestine or colon.

The prepared elastin biomaterial 10' may be used to repair portions of diseased or damaged vascular tissue, nonvascular tissue (e.g., esophagus, paracardium, lung, etc.) or as a skin layer replacement for use in burn or wound treatments. Internal wound repair is also is also an application. For instance, the elastin biomaterial 10' may also be used in organ reconstruction, e.g., molded in a pouch-like configuration for bladder reconstruction or shaped for esophageal replacement.

It may be desirable to use the elastin biomaterial 10' in combination with a supporting material having strong mechanical properties. For those applications, the elastin biomaterial 10' can be coated on the supporting material using various molding techniques described herein. Suitable supporting materials include polymers, such as woven polyethylene terepthalate (Dacron), teflon, polyolefin copolymer, polyurethane polyvinyl alcohol or other polymer. In addition, a polymer that is a hybrid between a natural polymer, such as fibrin and elastin, and a non-natural polymer such as a polyurethane, polyacrylic acid or polyvinyl alcohol may be used. Other prostheses that can be made from synthetics (or metals) and coated with the elastin biomaterial 10' (or from the biomaterial/synthetic hybrids) include cardiac valve rings and esophageal stents.

Once the elastin biomaterial 10' is prepared and formed into the desired shape, thickness and consistency it can be fused to tissue (or tissue substrates or other elastin biomaterial 10') utilizing vessel sealing technology.

Figure 2A:
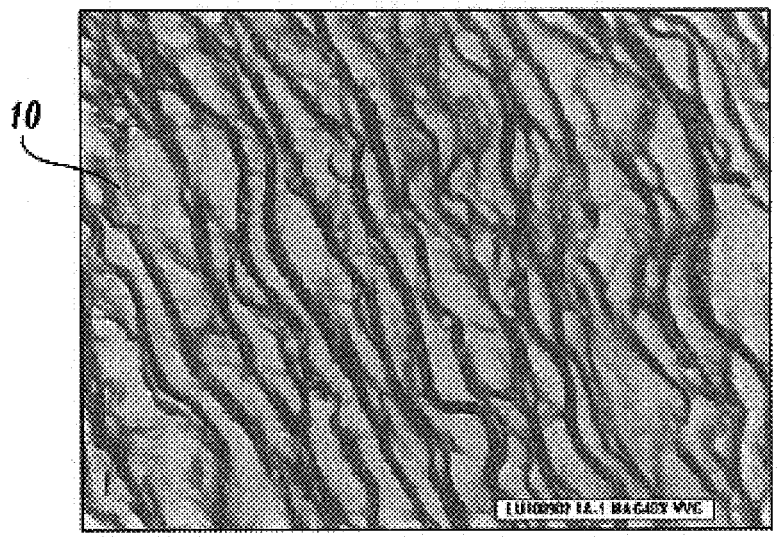
FIG. 2A is an enlarged, microscopic view (shown at 40× magnification) of the unsealed NaOH/Boiled aorta of FIG. 1C.
Figure 2B:
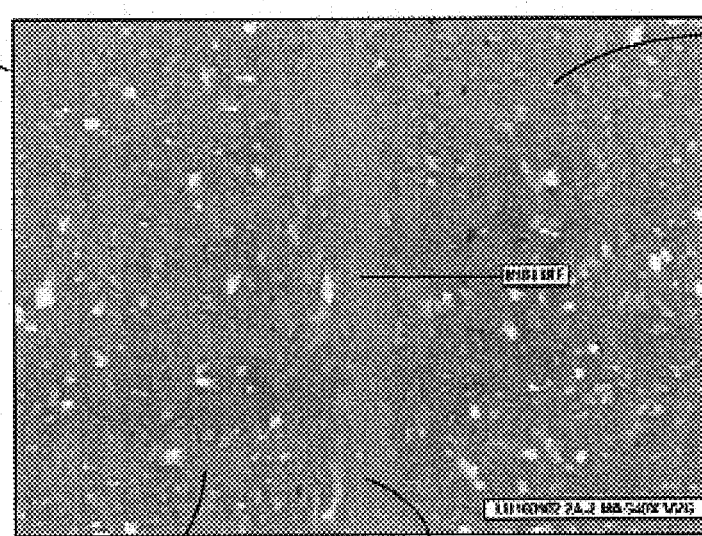
FIG. 2B is an enlarged, microscopic view (shown at 40× magnification) of 2 pieces of NaOH/Boiled aorta of FIG. 2A, after being sealed utilizing RF vessel sealing technology.

FIGS. 2A–2E show a resulting seal 20 between two elastin biomaterials 10a and 10b at various levels of magnification. More particularly, FIG. 2A shows the unsealed, boiled elastin 10 at 40× magnification prior to sealing. FIG. 2B shows two elastin biomaterial layers 10a and 10b at 40× magnification after sealing, illustrating a resulting seal 20a,b between these two elastin layers 10a and 10b. A comparison of FIGS. 2A and 2B shows a significant change in the elastin biomaterials 10a, 10b as a result of the sealing process. More particularly, the black elastin fibers have become condensed (i.e., fused) and individual fiber strands have become unrecognizable.

Figure 2C:
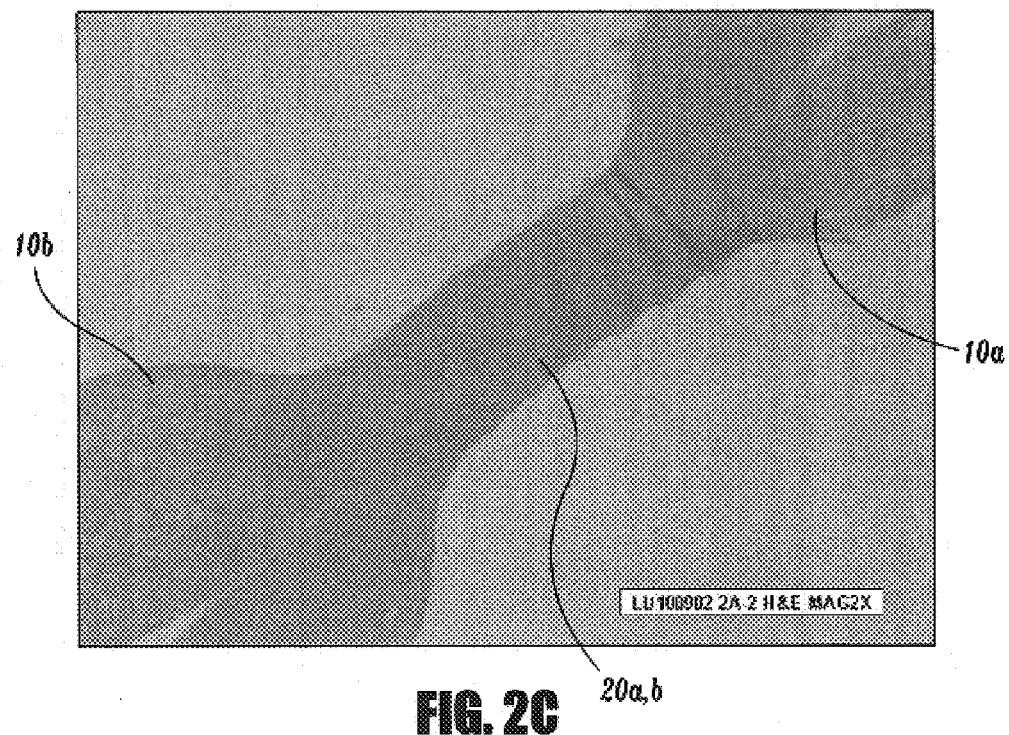
FIG. 2C is an enlarged, microscopic view (shown at 2× magnification) of FIG. 2B showing two layers of elastin biomaterial sealed together utilizing RF vessel sealing technology.
Figure 2D:
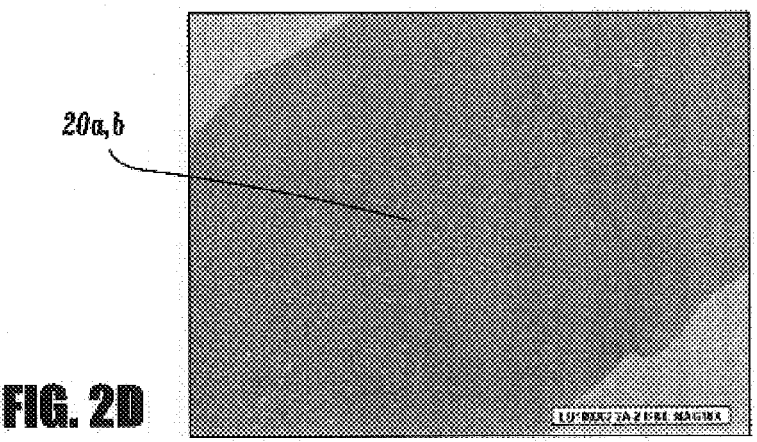
FIGS. 2D and 2E are enlarged, microscopic views of the sealing area between the two layers of elastin biomaterial of FIG. 2C under varying magnifications.
Figure 2E:
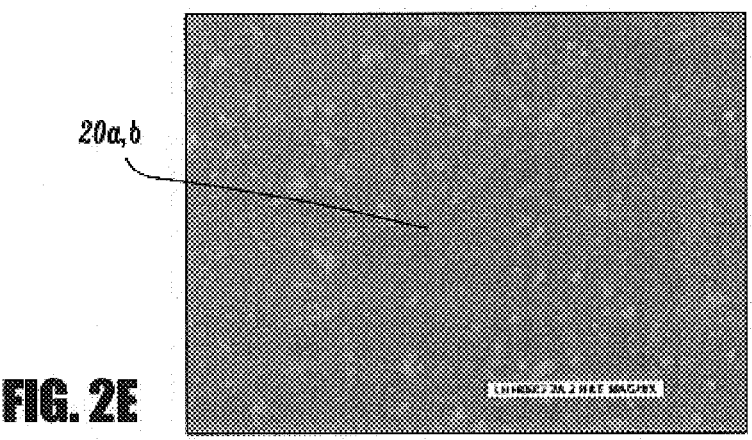

FIGS. 2C–2E show close-up views of the same seal 20a,b at 2× magnification, 1 × magnification and 40× magnification, respectively. The midline of the seal, i.e., where the two layers 10a and 10b of biomaterial come together, can be seen running diagonally in the lower right close-up of FIG. 2E.

It is envisioned that the elastin biomaterials 10' described herein may be fused to other tissues or other biomaterials. As mentioned above, vessel sealing utilizes a unique combination of controlled RF energy, pressure (within a specified pressure range) and specific gap distances between opposing tissue contacting surfaces to melt the elastin biomaterial 10' and tissue into a single mass (See FIG. 2B). These parameters must be carefully controlled to assure consistent and effective sealing/fusion of the elastin biomaterial 10'. Brief descriptions of various types of sealing instruments (i.e., open forceps and endoscopic forceps) which may be utilized to effectively seal elastin biomaterial 10' are included below with reference to FIGS. 3A–5E. More detailed descriptions of various vessel sealing instruments and various methods for sealing tissue are described in commonly-owned U.S. patent application Ser. No. 10/369,894 entitled "VESSEL SEALER AND DIVIDER AND METHOD MANUFACTURING SAME", U.S. patent application Ser. No. 10/460,926 entitled "VESSEL SEALER AND DIVIDER FOR USE WITH SMALL TROCARS AND CANNULAS", U.S. patent application Ser. No. 10/284,562 entitled "VESSEL SEALING INSTRUMENT" and U.S. patent application Ser. No. 10/284,562 entitled "BIPOLAR CONCENTRIC ELECTRODE ASSEMBLY FOR SOFT TISSUE FUSION" which are all incorporated by reference herein in their entirety.

Figure 3A:
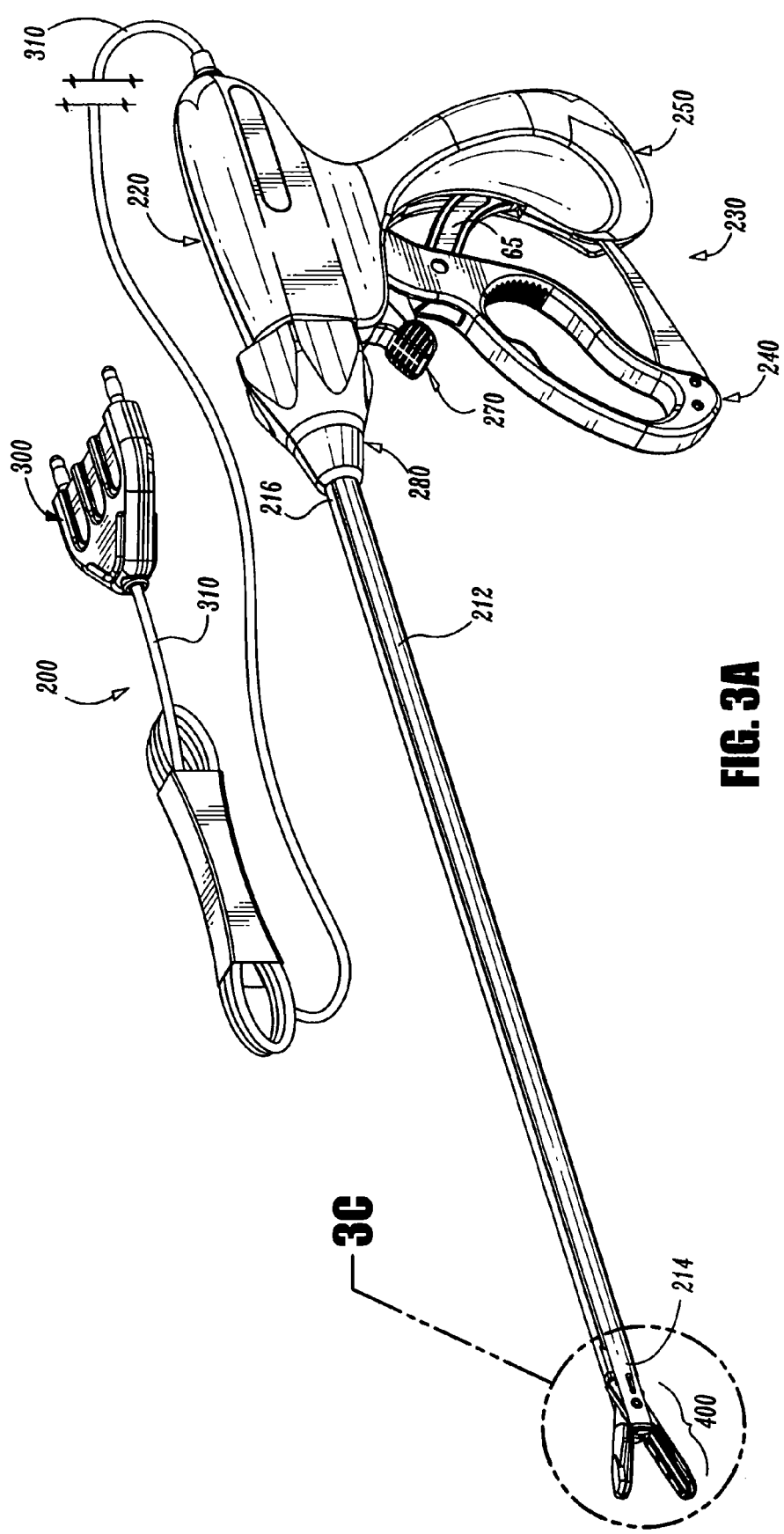
FIG. 3A is a side, perspective view of an endoscopic vessel sealing forceps for use with fusing elastin biomaterials according to the presently disclosed method.

FIG. 3A shows one example of an endoscopic vessel sealing instrument which may be employed for fusing the elastin biomaterials 10'. For the purposes herein, either an endoscopic instrument or an open instrument may be utilized for fusing elastin biomaterials. Obviously, different electrical and mechanical connections and considerations apply to each particular type of instrument and biomaterial, however, the novel aspects with respect to the electrode sealing assembly and its operating characteristics remain generally consistent with respect to both the open or endoscopic designs.

More particularly, FIG. 3A shows a sealing forceps 200 which generally includes a housing 220, a handle assembly 230, a rotating assembly 280, a trigger assembly 270 and an end effector assembly 400 which mutually cooperate to grasp, seal and, if warranted, divide tissue. The forceps 200 includes a shaft 212 which has a distal end 214 dimensioned to mechanically engage the end effector assembly 400 and a proximal end 216 which mechanically engages the housing 220. The proximal end 216 of shaft 212 is dimensioned to mechanically engage the rotating assembly 280.

Forceps 200 also includes a plug 300 which connects the forceps 200 to a source of electrosurgical energy, e.g., an electrosurgical generator (not shown) via an electrical cable 310. Handle assembly 230 includes a fixed handle 250 and a movable handle 240. Handle 240 moves relative to fixed handle 250 to actuate the end effector assembly 400 and enable a user to grasp and manipulate the elastin biomaterial 10'. More particularly, the end effector assembly 400 includes a pair of opposing jaw members 410 and 420 which move in response to movement of handle 240 from an open position wherein the jaw members 410 and 420 are disposed in spaced relation relative to one another, to a clamping or closed position wherein the jaw members 410 and 420 cooperate to grasp elastin biomaterial 10' and tissue substrate 900 therebetween (See FIG. 5B).

Figure 3B:
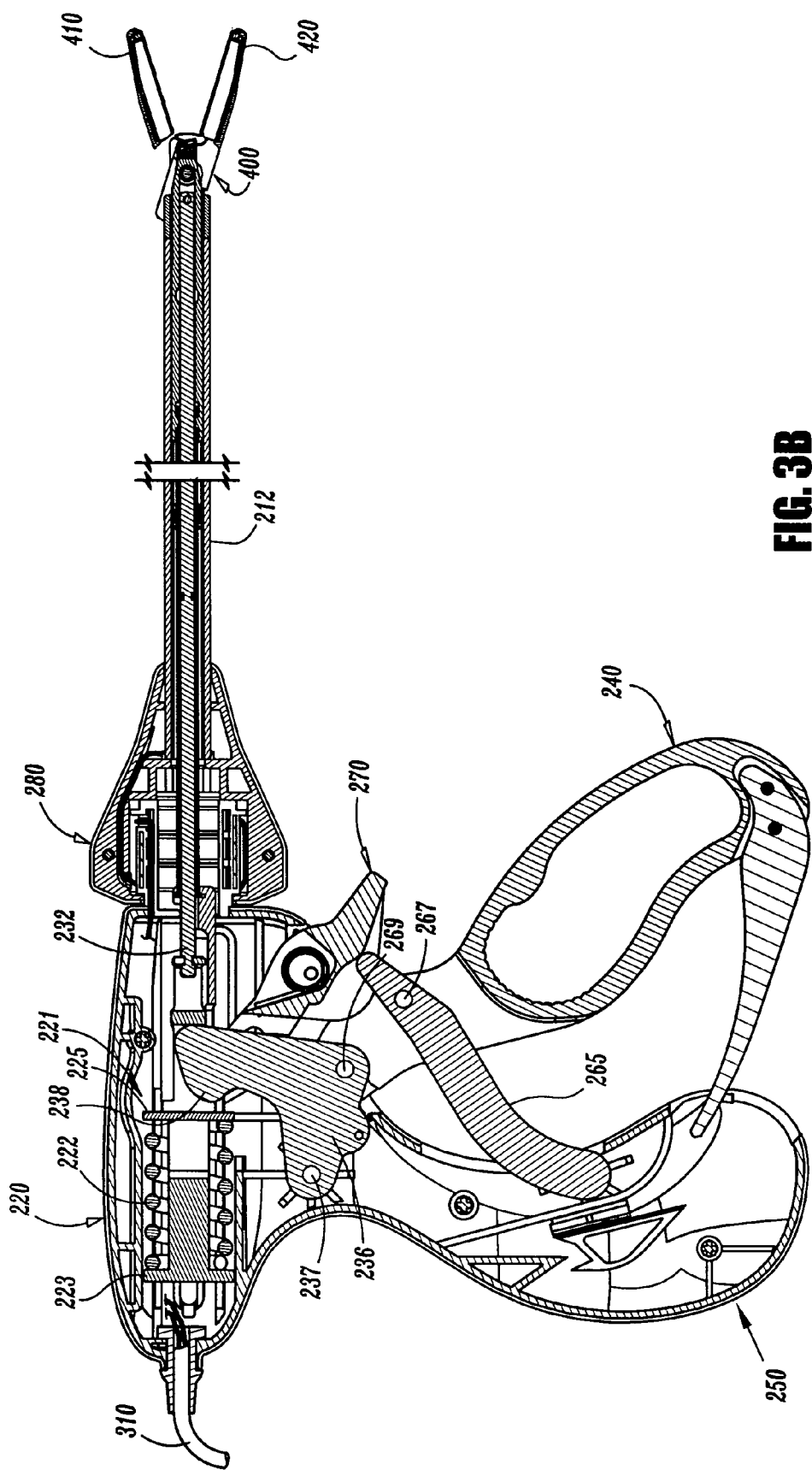
FIG. 3B is a side, cross section of the forceps of FIG. 3A.

As best shown in FIG. 3B, the housing 220 encloses a drive assembly 221 which cooperates with the movable handle 240 to impart movement of the jaw members 410 and 420 from the open position to the clamping or closed position. The handle assembly 230 can generally be characterized as a four-bar mechanical linkage composed of the following elements: movable handle 240, a link 265, a cam-like link 236 and a base link embodied by fixed handle 250 and a pair of pivot points 267 and 269. Movement of the handle 240 activates the four-bar linkage which, in turn, actuates the drive assembly 221 for imparting movement of the opposing jaw members 410 and 420 relative to one another to grasp elastin biomaterial 10' therebetween.

As best shown in FIGS. 3C and 3D, each jaw member 410, 420 includes a jaw housing 416, 426, an insulative substrate or insulator 414, 424 and an electrically conducive surface 412, 422. Insulators 414, 424 may be securely engaged to the electrically conductive sealing surface by stamping, overmolding, overmolding a stamped electrically conductive sealing plate and/or overmolding a metal injection molded seal plate. All of these manufacturing techniques produce electrodes having an electrically conductive surfaces 412, 422 which are substantially surrounded by insulating substrates 414, 424. Each insulator's 414, 424 electrically conductive sealing surface 412, 422 and the outer, non-conductive jaw housing 416, 426 are dimensioned to limit and/or reduce many of the known undesirable effects related to sealing, e.g., flashover, thermal spread and stray current dissipation. The jaw members 410 and 420 are electrically isolated from one another such that electrosurgical energy can be effectively transferred to electrically conductive surfaces 412 and 422 and through the elastin biomaterial 10' to form a seal.

As the handle 240 is squeezed, the cam link 236, through the mechanical advantage of the four-bar mechanical linkage, is rotated generally proximally about pivots 237 and 269 such that the cam piston 238 biases tab 225 to compress spring 222 against flange 223. Simultaneously, drive rod 232 is pulled proximally which, in turn, causes cam pin 470 (See FIGS. 3C and 3D) to move proximally and close the jaw members 410 and 420 relative to one another. The jaw members 410 and 420 may be opened, closed and rotated to manipulate the elastin biomaterial 10' until sealing is desired. This enables the user to position and re-position the forceps 200 prior to activation and sealing.

A series of stop members 150a, 150b and 150c is preferably disposed on the inner facing surfaces of the electrically conductive sealing surfaces 412 and 422 to facilitate gripping and manipulation of the elastin biomaterial 10' and to define a gap "G" (See FIG. 5B) between opposing jaw members 410 and 420 during sealing. As best seen in FIGS. 3C and 3D, in order to achieve a desired spacing between the electrically conductive surfaces 412 and 422 of the respective jaw members 410, 420, (i.e., gap distance) and apply a desired force to seal the tissue to the biomaterial, at least one jaw member 410 and/or 420 includes stop member(s), e.g., 150a, 150b and 150c which limit the movement of the two opposing jaw members 410 and 420 relative to one another. The stop member(s), e.g., 150a, extends from the sealing surface or tissue contacting surface 422 a predetermined distance according to the specific material properties of the stop members 150a (e.g., compressive strength, thermal expansion, etc.) to yield a consistent and accurate gap distance during sealing. The gap distance between opposing sealing surfaces 412, 422 during sealing of biomaterials preferably ranges from about 0.004 inches to about 0.010 inches.

Stop members 150a–150c are preferably made from an insulative material, e.g., parylene, nylon and/or ceramic, and are dimensioned to limit opposing movement of the jaw members 410 and 420 to within the above-mentioned gap range. The stop members 150a–150c can be disposed on one or both of the jaw members 410 and 420 and may be dimensioned in a variety of different shapes and sizes, longitudinal, circular, ridge-like, etc.

The non-conductive stop members 150a–150c are molded onto the jaw members 410 and 420 (e.g., overmolding, injection molding, etc.), stamped onto the jaw members 410 and 420, deposited (e.g., deposition) onto the jaw members 410 and 420 and/or thermally sprayed onto the surface of the jaw members 410 and 420 (e.g., a ceramic material may be thermally sprayed) to form the stop members 150a–150c. Many different configurations for the stop members 150a–150c are discussed in detail in commonly-assigned, co-pending U.S. application Ser. No. PCT/US01/11413 entitled "VESSEL SEALER AND DIVIDER WITH NON-CONDUCTIVE STOP MEMBERS" by Dycus et al. which is hereby incorporated by reference in its entirety herein.

Once the desired position for the sealing site is determined and the jaw members 410 and 420 are properly positioned, handle 240 may be compressed fully to lock the jaw members 410 and 420 in a closed position against the elastin biomaterial 10' and tissue substrate/other biomaterial. The details for locking the handle 240 with respect to handle 250 are disclosed in commonly-owned U.S. patent application Ser. No. 10/369,894 entitled "VESSEL SEALER AND DIVIDER AND METHOD MANUFACTURING SAME" which is incorporated in its entirety by reference herein. When the jaw members 410 and 420 are fully compressed about the elastin biomaterial 10' and tissue substrate (or other biomaterial) the forceps 200 is now ready for selective application of RF energy.

Experimental results suggest that the magnitude of pressure exerted on the elastin biomaterial 10' by the seal surfaces 412 and 422 is important in assuring a proper surgical seal. Pressures within a working range of about 3 kg/cm$^2$ to about 16 kg/cm$^2$ and, preferably, within a working range of 4.5 kg/cm$^2$ to 8.5 kg/cm$^2$ have been shown to be effective for sealing various tissue types. In addition to keeping the pressure within a working range (i.e., about 3 kg/cm$^2$ to about 16 kg/cm$^2$) and the gap distance within a specified range (i.e., about 0.004 inches to about 0.010 inches) the electrical power should be kept within the range of about 1 W to about 350 W, about 1 Vrms to about 400 Vrms and about 0 Amps to about 5.5 Amps. Moreover, the electrodes and/or the sealing surfaces 412 and 422 should be designed for low thermal mass to optimize thermal heating between jaw members 410 and 420 and minimize thermal loss through the device.

Preferably, the four-bar handle assembly 230, spring 222 and drive assembly 221 are manufactured and dimensioned such that the cooperation of these working elements, i.e., the four-bar handle assembly 230 (and the internal working components thereof), the spring 222 and drive assembly 221, maintain tissue pressures within the above working ranges. Alternatively, the handle assembly 230, the spring 222 or the drive assembly 221 may be manufactured and dimensioned to produce pressures within the above working range independently of the dimensions and characteristic of the other of these working elements. One such handle assembly is described in commonly-owned U.S. patent application Ser. No. 10/369,894 entitled "VESSEL SEALER AND DIVIDER AND METHOD MANUFACTURING SAME"

By controlling the intensity, frequency and duration of the RF energy applied to the elastin biomaterial 10', the user can selectively seal the elastin biomaterial 10' as needed for a particular purpose. As can be appreciated, various biomaterials and the physical characteristics associated with each biomaterial and the particular purpose of the biomaterial may require unique sealing electrical parameters. It is envisioned that the above forceps 200 may be utilized in connection with a closed-loop RF control system which optimizes sealing based upon pre-surgical conditions or changes in physical or electrical conditions during sealing. One example of a closed-loop control system is described in commonly-owned and concurrently-filed U.S. patent application Ser. No. 10/427,832 entitled "METHOD AND SYSTEM FOR CONTROLLING OUTPUT OF RF MEDICAL GENERATOR" and commonly-owned and concurrently-filed U.S. Patent Application Ser. No. filed as U.S. Provisional Application 60/466,954] entitled "METHOD AND SYSTEM FOR PROGRAMMING AND CONTROLLING AN ELECTROSURGICAL GENERATOR SYSTEM" which are both incorporated in their entirety by reference herein. In general, the closed-loop control, system includes a user interface for allowing a user to select at least one pre-surgical parameter, such as the type of surgical instrument operatively connected to the generator, the type of tissue and/or a desired surgical effect. A sensor module is also included for continually sensing at least one of electrical and physical properties proximate the surgical site and generating at least one signal relating thereto.

The closed loop control system also includes a control module for continually receiving or monitoring surgical parameters and each of the signals from the sensor module and processing each of the signals in accordance with a desired surgical effect using a microprocessor, computer algorithm and/or a look-up table. The control module generates at least one corresponding control signal relating to each signal from the sensor module, and relays the control signal to the electrosurgical generator for controlling the generator. The closed loop system may be employed in a feedback circuit or part of a surgical method for optimizing a surgical seal. The method includes the steps of: applying a series of electrical pulses to the surgical site; continually sensing electrical and physical properties proximate the surgical site; and varying pulse parameters of the individual pulses of the series of pulses in accordance with the continually-sensed properties.

As mentioned above, it is also contemplated that the sealing surfaces 412 and 422 of the jaw members 410 and 420 can be made from or coated with non-stick materials. When utilized on the sealing surfaces 412 and 422, these materials provide an optimal surface energy for eliminating sticking due in part to surface texture and susceptibility to surface breakdown due to electrical effects and corrosion in the presence of biologic tissues. It is envisioned that these materials exhibit superior non-stick qualities over stainless steel and should be utilized on the forceps 200 in areas where the exposure to pressure and RF energy can create localized "hot spots" more susceptible to tissue adhesion. As can be appreciated, reducing the amount that biomaterials 10' "stick" during sealing improves the overall efficacy of the instrument. The non-stick materials may be manufactured from one (or a combination of one or more) of the following "non-stick" materials: nickel-chrome, chromium nitride, MedCoat 2000, Inconel 600 and tin-nickel.

For example, high nickel chrome alloys, Ni200, Ni201 (~100% Ni) may be made into electrodes or sealing surfaces by metal injection molding, stamping, machining or any like process. Also and as mentioned above, the sealing surfaces 412 and 422 may also be "coated" with one or more of the above materials to achieve the same result, i.e., a "non-stick surface". One particular class of materials disclosed herein has demonstrated superior non-stick properties and, in some instances, superior seal quality. For example, nitride coatings which include, but not are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reduce overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 412 and 422 made from or coated with Ni200, Ni201 (~100% Ni) also showed improved non-stick performance over typical bipolar stainless steel electrodes.

Figure 4A:
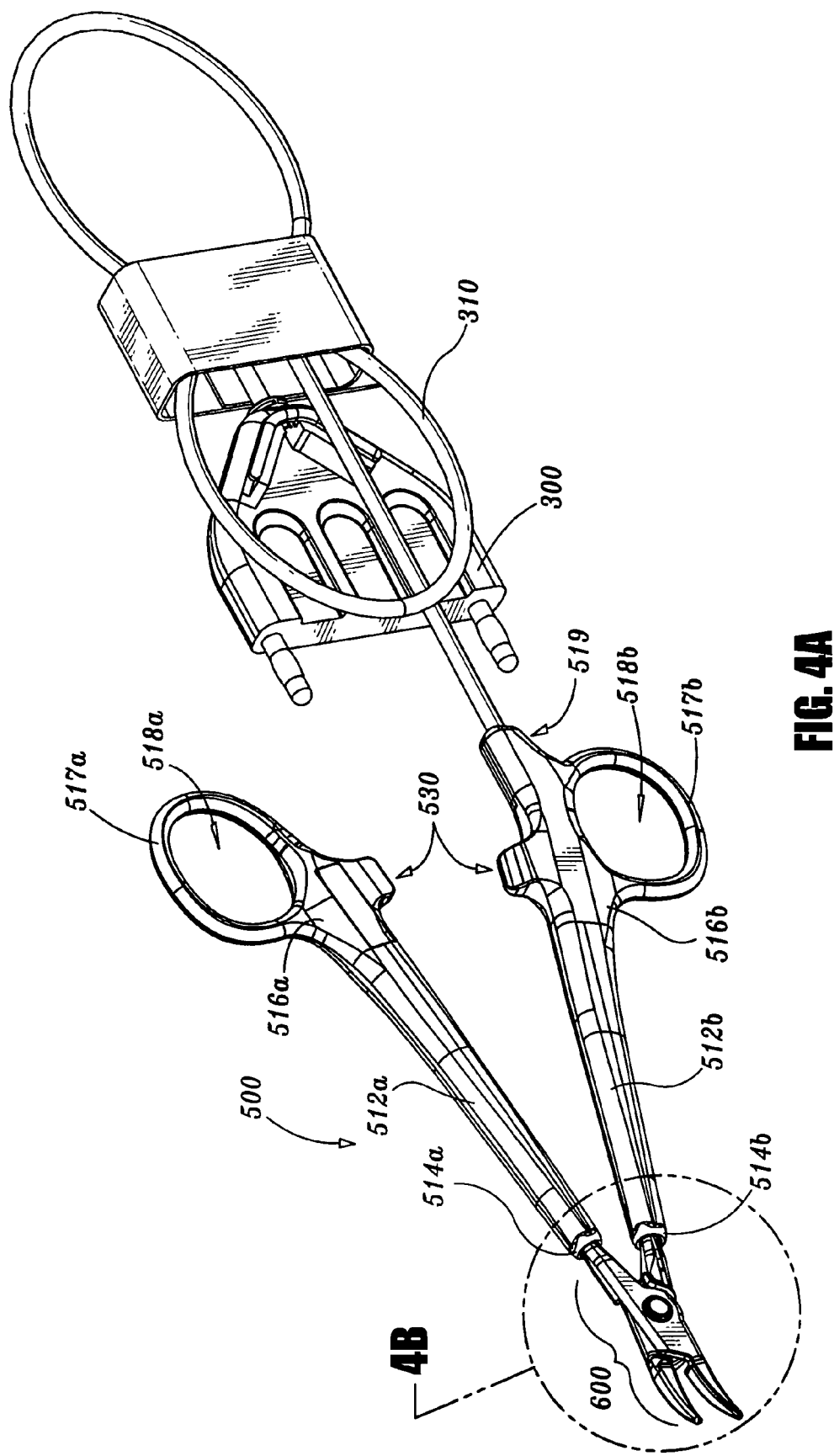
FIG. 4A is a side, perspective view of an open vessel sealing forceps for use with fusing elastin biomaterials according to the presently disclosed method.

An open forceps 500 is also contemplated for use in connection with traditional open surgical procedures and is shown by way of example in FIG. 4A. Open forceps 500 includes a pair of elongated shaft portions 512a, 512b each having a proximal end 516a and 516b, respectively, and a distal end 514a and 514b, respectively. The forceps 500 includes jaw assembly 600 which attaches to the distal ends 514a and 514b of shafts 512a and 512b, respectively. Jaw assembly 600 includes opposing jaw members 610 and 620 which are pivotably connected about a pivot pin 650 (See FIGS. 4B and 4C).

Preferably, each shaft 512a and 512b includes a handle 517a and 517b disposed at the proximal end 516a and 516b thereof which each define a finger hole 518a and 518b, respectively, therethrough for receiving a finger of the user. As can be appreciated, finger holes 518a and 518b facilitate movement of the shafts 512a and 512b relative to one another which, in turn, pivot the jaw members 610 and 620 from an open position wherein the jaw members 610 and 620 are disposed in spaced relation relative to one another for manipulating tissue to a clamping or closed position wherein the jaw members 610 and 620 cooperate to grasp elastin biomaterial 10' and tissue substrate therebetween. A ratchet 530 is preferably included for selectively locking the jaw members 610 and 620 relative to one another at various positions during pivoting.

Preferably, each position associated with the cooperating ratchet interfaces 530 holds a specific, i.e., constant, strain energy in the shaft members 512a and 512b which, in turn, transmits a specific closing force to the jaw members 610 and 620. It is envisioned that the ratchet 530 may include graduations or other visual markings which enable the user to easily and quickly ascertain and control the amount of closure force desired between the jaw members 610 and 620. One of the shafts, e.g., 512b, includes a proximal shaft connector/flange 519 which is designed to connect the forceps 500 to a source of RF energy (not shown) via an electrosurgical cable 310 and plug 300.

Figure 4B:
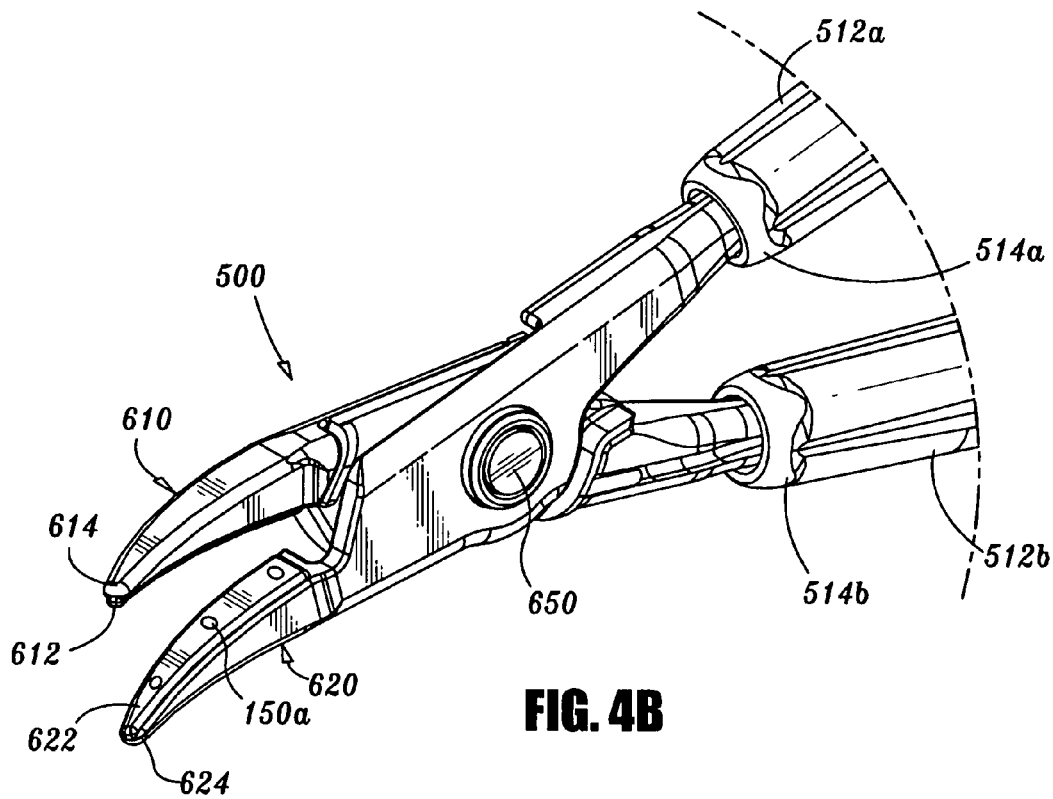
FIG. 4B is an enlarged, side, perspective view of an end effector of the forceps of FIG. 4A shown in an open configuration.
Figure 4C:
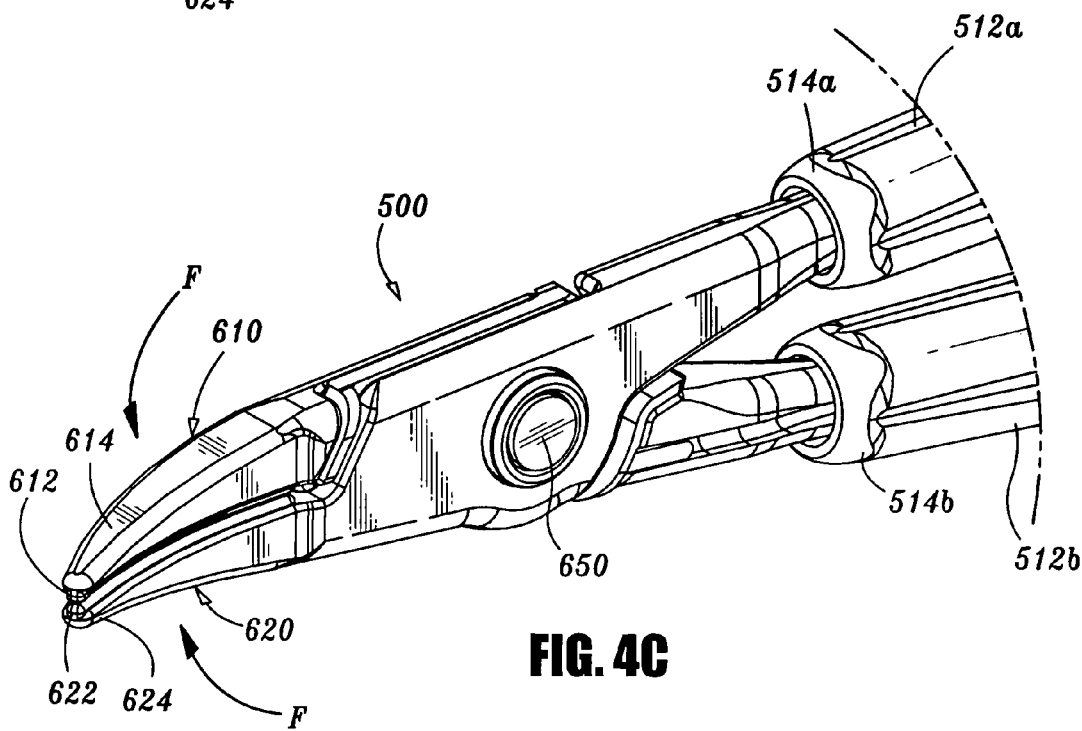
FIG. 4C is an enlarged, side, perspective view of the end effector of the forceps of FIG. 4A shown in a closed configuration.
Figure 5B:
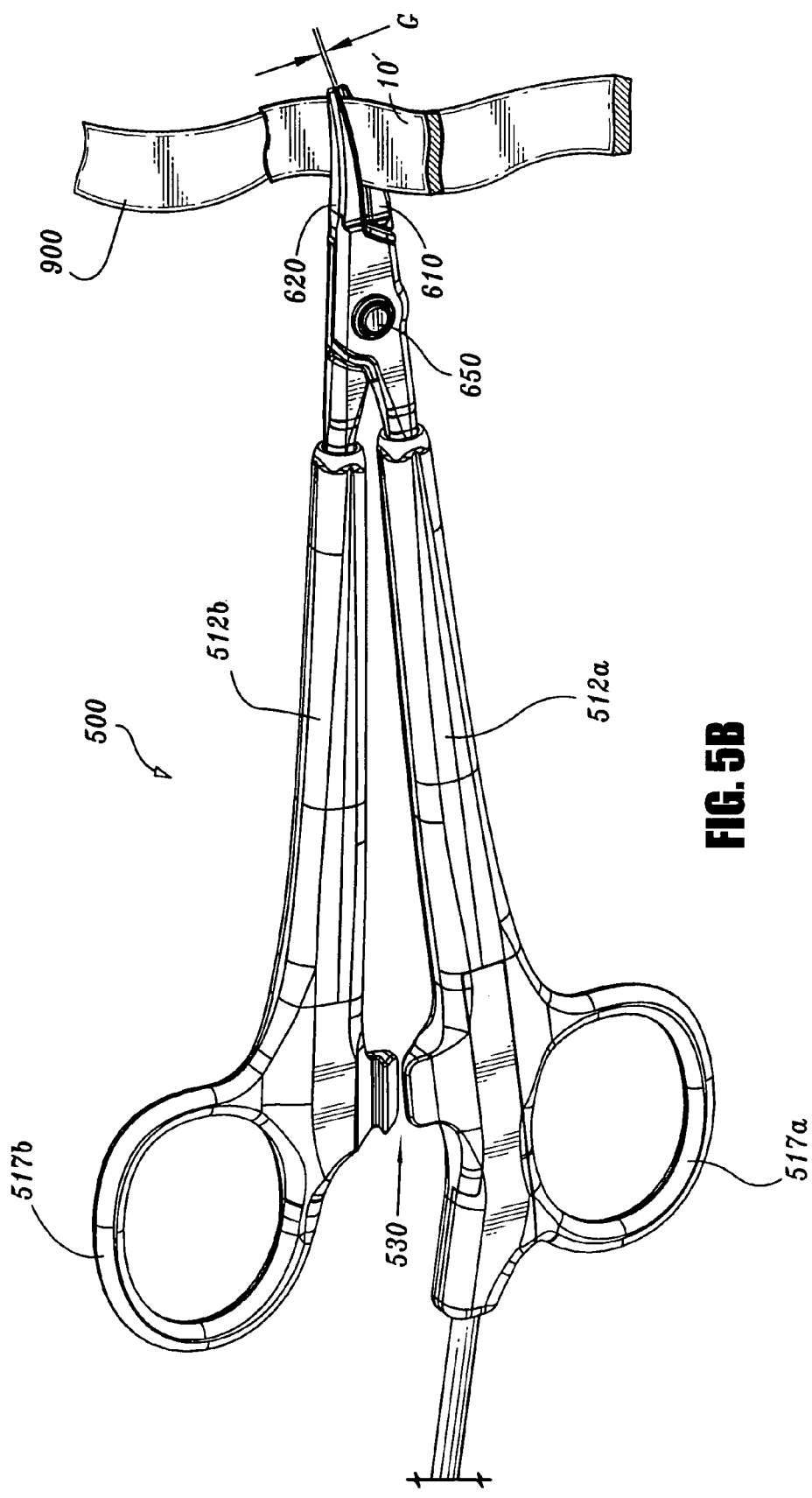
FIG. 5B is a side, perspective view of the forceps of FIG. 4A shown with tissue and biomaterial grasped between opposing jaw members and a gap distance being maintained between opposing jaw surfaces.

As best seen in FIGS. 4B and 4C, the two opposing jaw members 610 and 620 are generally symmetrical and include similar component features which cooperate to permit facile rotation about pivot pin 650 to effect the grasping and sealing of elastin biomaterial 10' and tissue substrate 900 (See FIG. 5B). Jaw member 610 includes an insulated outer housing 614 which is dimensioned to mechanically engage an electrically conductive sealing surface 612. Preferably, outer insulative housing 614 extends along the entire length of jaw member 610 to reduce alternate or stray current paths during sealing and/or incidental burning of elastin biomaterial 10' or the underlying tissue substrate. Likewise, jaw member 620 includes similar elements which include an outer housing 624 which engages an electrically conductive sealing surface 622 and an electrically conductive sealing surface 622.

Much like the aforedescribed endoscopic forceps of FIGS. 3A–3C, the jaw members 610 and 620 of the open forceps 500 also include at least one stop member 150a disposed on the inner facing surface of the electrically conductive sealing surface 612 (and/or 622). Alternatively or in addition, the stop member 150a may be positioned adjacent to the electrically conductive sealing surfaces 612, 622 or proximate the pivot pin 650. The stop member(s) is preferably designed to define a gap "G" (See FIG. 5B) between opposing jaw members 610 and 620 during this type of sealing. Preferably the separation distance during sealing or the gap distance "G" is within the range of about 0.004 inches (~0.1016 millimeters) to about 0.010 inches (~0.254 millimeters).

As mentioned above, two mechanical factors play an important role in determining the resulting thickness of the sealed elastin biomaterial 10' and effectiveness of the seal, i.e., the pressure applied between opposing jaw members 610 and 620 and the gap "G" between the opposing jaw members 610 and 620 during the sealing process. Applying the correct force is also important for other reasons: to reduce the impedance of the elastin biomaterial 10' (and/or elastin biomaterial 10' and tissue substrate) to a low enough value that allows enough current through the elastin biomaterial 10'; and to overcome the forces of expansion during the heating of the elastin biomaterial 10' in addition to contributing towards creating the required seal thickness necessary for a satisfactory seal.

Insulated outer housing 614 is dimensioned to securely engage the electrically conductive sealing surface 612. It is envisioned that this may be accomplished by stamping, by overmolding, by overmolding a stamped electrically conductive sealing plate and/or by overmolding a metal injection molded seal plate. All of these manufacturing techniques produce an electrode having an electrically conductive surface 612 which is substantially surrounded by an insulated outer housing 614. The insulated outer housing 614 and the electrically conductive sealing surface 612 are preferably dimensioned to limit and/or reduce many of the known undesirable effects related to sealing, e.g., flashover, thermal spread and stray current dissipation. These and other envisioned embodiments are discussed in commonly-assigned Application Ser. No. PCT/US01/11412 entitled "ELECTROSURGICAL INSTRUMENT WHICH REDUCES COLLATERAL DAMAGE TO ADJACENT TISSUE" by Johnson et al. and commonly-assigned Application Ser. No. PCT/US01/11411 entitled "ELECTROSURGICAL INSTRUMENT WHICH IS DESIGNED TO REDUCE THE INCIDENCE OF FLASHOVER" by Johnson et al.

As mentioned above with respect to forceps 200, it is also contemplated that the forceps 500 (and/or the electrosurgical generator used in connection with the forceps 500) may include an RF closed loop system, sensor or feedback mechanism (not shown) which automatically selects the appropriate amount of RF energy to effectively seal the particular elastin biomaterial 10') and/or elastin biomaterial 10' and tissue substrate) grasped between the jaw members 610 and 620. The sensor or feedback mechanism may also measure the impedance across the elastin biomaterial 10' during sealing and provide an indicator (visual and/or audible) that an effective seal has been created between the jaw members 610 and 620.

Other embodiments of electrode assemblies are envisioned such as the electrode assemblies described in commonly-owned PCT Patent Application Serial No. PCT/US03/08146 entitled "BIPOLAR CONCENTRIC ELECTRODE CONFIGURATION FOR SOFT TISSUE FUSION" which is incorporated in its entirety by reference herein. FIGS. 5C–5E generally show various concentric electrode configurations described in the above-identified disclosure which include an array of electrode micro-sealing pads 800 disposed across one or both jaw members 710 and 720. It is envisioned that the array of micro-sealing pads 800 essentially spot weld areas of tissue between the micro-sealing pads 800 while allowing other tissue areas (i.e., tissue not contained between the micro-sealing pads) remains viable. As can be appreciated this promotes tissue healing.

More particularly, the electrical paths from the array of electrode micro-sealing pads 800 are preferably mechanically and electrically interfaced with corresponding electrical connections disposed within shafts 214a and 214b. For example and with respect to FIG. 5E, a first electrical path 726 having a first electrical potential is connected to each ring electrode 820 of each electrode micro-sealing pad 800 and a second electrical path 716 having a second electrical potential is connected to each post electrode 830 of each electrode micro-sealing pad 800. As can be appreciated, the jaw members 710 and 720 include non-conductive contacting surfaces 784, 786, respectively, and an array of micro-sealing pads 800 disposed substantially along the entire longitudinal length of each respective jaw member 710 and 720. Preferably, the non-conductive contacting surfaces 784, 786 are made from an insulative material such as ceramic, or, alternatively, the non-conductive tissue contacting surfaces 784, 786 may be made from a material or a combination of materials having a high Comparative Tracking Index (CTI).

One or more stop members 150a and 150b may be positioned adjacent to the non-conductive sealing surfaces 784, 786 or proximate pivot 750. Much like the embodiments described above, the stop members 150a and 150b are designed to define a gap "G" (See FIG. 5B) between opposing jaw members 710 and 720 during the sealing process. It is envisioned that the array of electrode micro-sealing pads 800 may also act as stop members for regulating the distance "G" between opposing jaw members 710 and 720.

As best shown in FIG. 5C, the electrode micro-sealing pads 500 may be arranged in longitudinal, pair-like fashion along the jaw members 710 and/or 720. The micro-sealing pads may be disposed on a single jaw member, e.g., 710, or on both jaw members 710 and 720. Alternatively, one jaw member, e.g., 710, may include a ring electrode 820 and the other jaw member 720 may include a post electrode 830. As such and as identified in FIG. 5E, each post electrode 830 and the opposing ring electrode 820 together define one electrode micro-sealing pad 800.

Preferably, the post electrode 830 is concentrically centered opposite the ring electrode 820 such that when the jaw members 710 and 720 are closed about the elastin biomaterial 10' (and/or elastin biomaterial 10' and tissue substrate 900), RF energy flows from the ring electrode 820, through tissue and to the post electrode 830. Insulating materials 814 and 824 isolate the electrodes 820 and 830 and prevent stray current tracking to surrounding tissue areas.

A controller (not shown) may be electrically interposed between the generator 350 and the electrodes 820, 830 to regulate the RF energy supplied thereto depending upon certain electrical parameters, i.e., current impedance, temperature, voltage, etc. For example, the instrument or the controller may include one or more smart sensors (not shown) which communicate with the electrosurgical generator 350 (or smart circuit, computer, feedback loop, etc.) to automatically regulate the electrical intensity (waveform, current, voltage, etc.) to enhance the micro-sealing process. The sensor may measure or monitor one or more of the following parameters: temperature, impedance at the microseal, change in impedance over time and/or changes in the power or current applied over time. An audible or visual feedback monitor (not shown) may be employed to convey information to the surgeon regarding the overall micro-seal quality or the completion of an effective micro-seal. Examples of a various control circuits, generators and algorithms which may be utilized are disclosed in commonly-owned U.S. Pat. No. 6,228,080 and U.S. application Ser. No. 10/073,761 entitled "VESSEL SEALING SYSTEM" the entire contents of both of which are hereby incorporated by reference herein.

During sealing, an intermittent pattern of individual micro-seals is created along and across the elastin biomaterial 10' and tissue substrate 900. The arrangement of the micro-sealing pads 800 across the jaws 710 and 720 only seals the elastin biomaterial 10' and tissue substrate 900 which is between each micro-sealing pad 800. The adjacent elastin biomaterial 10' (and/or tissue substrate 900) remains viable which, as can be appreciated, allows blood and nutrients to flow through the sealing site and between the individual micro-seals to promote healing and reduce the chances of tissue necrosis. By selectively regulating the closure pressure, gap distance "G", and electrosurgical intensity, effective and consistent micro-seals may be created for many different types of biomaterials. For example, it is also envisioned that the pattern and/or density of the micro-sealing pads 800 may be configured along a jaw member 710 and/or 720 to seal different types or thicknesses of elastin biomaterial 10'.

Experimental results suggest that the magnitude of pressure exerted by the micro-sealing pads 800 is important in assuring a proper surgical outcome, maintaining tissue viability. Pressures within a working range of about 3 kg/cm$^2$ to about 16 kg/cm$^2$ and, preferably, within a working range of about 4.5 kg/cm$^2$ to about 8.5 kg/cm$^2$ have been shown to be effective for micro-sealing. The micro-sealing pads 800 may be arranged in many different configurations across or along the jaw members 710 and 720 depending upon a particular purpose.

FIG. 5A shows the two opposing jaw members 610 and 620 of the open forceps 500 poised for grasping an elastin patch 10' and tissue 900 (or other biomaterial or other elastin 10') prior to activation and sealing. More particularly and as described in detail above, once the elastin biomaterial 10' is prepared and formed into the desired shape, thickness and consistency it can be fused to tissue 900 (or other biomaterial) utilizing one or more of the above described vessel sealing devices, namely, endoscopic forceps 200, open forceps 500 or 700. The unique combination of controlled RF energy, pressure (within a specified pressure range) and specific gap distances between opposing tissue contacting surfaces melt the elastin biomaterial 10' and tissue 900 into a single mass. FIG. 5B shows the open forceps 500 in a substantially closed position about a patch of elastin 10' and tissue 900 prior to sealing. As can be appreciated, the opposing jaw members 610 and 620 maintain a specific gap distance "G" necessary for effective sealing of the elastin patch 10' and the tissue 900.

Utilizing the inherent electrical, thermal and physical properties of the elastin biomaterial 10' and tissue 900 coupled with the unique attributes associated with the above-described vessel sealing instruments 200, 500 and 700 (i.e., pressure, gap, RF energy control, electrode design, etc.), a fluid tight, hemostatic and structured fuse is created. It is envisioned that the resulting fuse between the elastin 10' and the tissue 900 is fairy homogeneously with only slight demarcation between the two layers (See FIG. 2B). Moreover and unlike laser welding, energy absorbing dyes, e.g., indocyanine green, are not necessary to control or regulate the fusing process.

It is envisioned that the elastin biomaterial 10' may be secured or fused to tissue substrates, soft tissue (lung, intestine, bowel, blood vessels, muscles, skin, etc.) or other biomaterials as a means for tissue healing, reconstruction, repair and replacement. As mentioned above, sheets or patches of elastin biomaterial 10' may be selectively varied in size, thickness and shape and/or may be formed into molds (tubular or otherwise) and scaffolding depending upon the intended purpose for the elastin biomaterial 10'. As a result, the elastin biomaterial 10' may be used to repair portions of diseased or damaged vascular tissue, nonvascular tissue (e.g., esophagus, paracardium, lung, etc.) or as a skin layer replacement for use in burn or wound treatments. In addition, the elastin biomaterial 10' may also be used in organ reconstruction, e.g., molded in a pouch-like configuration for bladder reconstruction or shaped for esophageal replacement.

Figure 6A:
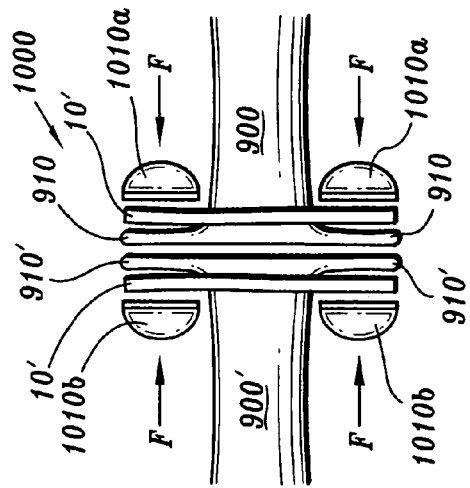
FIGS. 6A and 6B are schematic representations of two gasket-shaped biomaterials being fused between two opposing jaw members to perform an end-to-end anastomosis.
Figure 6B:
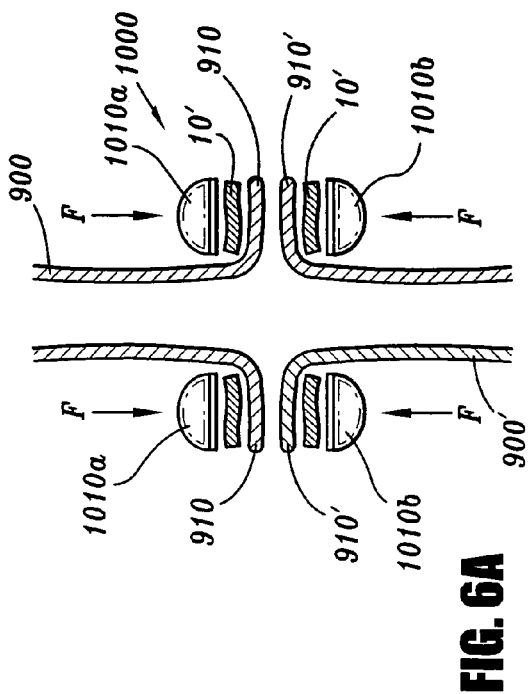

FIGS. 6A–6B and 7A–7B show envisioned methods of using the elastin patch 10' for creating an end-to-end anastomosis of two vessel segments 900 and 900'. More particularly, FIGS. 6A and 6B show a schematic representation of a general circular anastomosis vessel sealing instrument 1000 having opposing jaw members 1010a and 1010b. The two vessel segments 900 and 900' are preferably everted to expose the vessel intima 910 and 910', respectively. The vessel intimas 910 and 910' are juxtaposed and two rings of elastin biomaterial 10' are positioned about each vessel segment 900 and 900' on an external side thereof. The opposing jaw members 1010a and 1010b are then positioned on either side of the two vessel segments 900 and 900' with the elastin biomaterial 10' disposed therebetween. The jaw members 1010a and 1010b are then compressed about the elastin 10' and the tissue 900 and 900' (e.g., with a force "F" within the preferred working range of about 3 kg/cm$^2$ to about 16 kg/cm$^2$ or, preferably, about 4.5 kg/cm$^2$ to about 8.5 kg/cm$^2$) to form a seal.

It is envisioned that the two elastin 10' rings and the two vessels 900 and 900' reforms into a single fused mass and/or that the elastin material 10' alone reform into a fused mass to hold the anastomosis. In either instance, the resulting anastomosis remains intact.

Figure 7A:
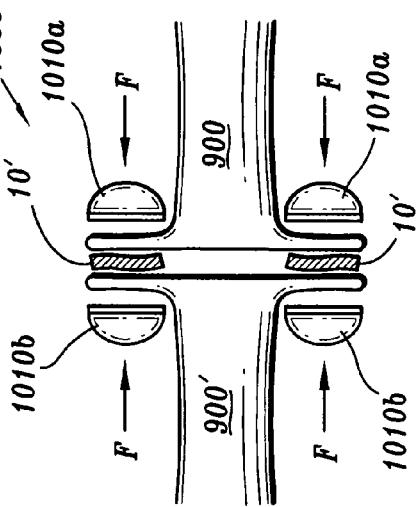
FIGS. 7A and 7B are schematic representations of one gasket-shaped biomaterial being fused between everted tissue ends by two jaw members to perform an end-to-end anastomosis.
Figure 7B:
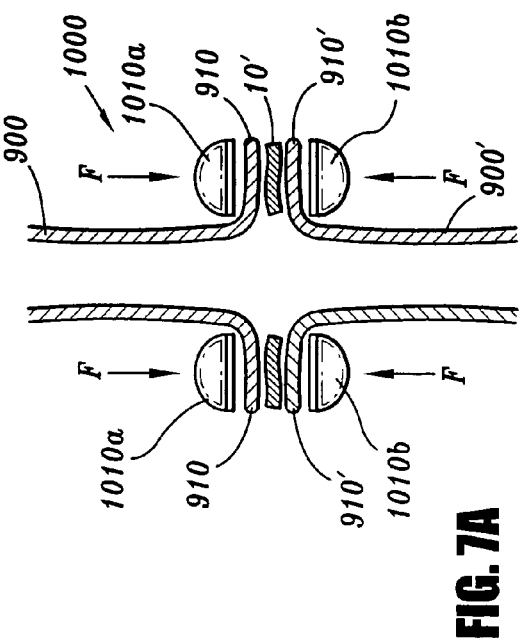

FIGS. 7A–7B show an alternate method of performing an end-to-end anastomosis wherein the elastin biomaterial 10' is positioned between the intimal, abutting surfaces 910 and 910' of the two vessels 900 and 900', respectively. Much in the same fashion as described above, the two jaw members 1010a and 1010b are positioned about the vessels 900 and 900' and compressed to form a seal. Again, the elastin biomaterial 10' and the two vessels 900 and 900' reform into a fused mass.

Alternatively, the biomaterial 10' may be fused directly with a vessel 900. More particularly, FIGS. 9A and 9B show a schematic representation of a circular anastomosis similar to the above figures wherein a vessel segment 900 and segment of biomaterial 10' are everted to expose their respective intimas 910 and 10". The vessel intimas 910 and 10" are juxtaposed and on their external sides and the opposing jaw members 1010a and 1010b are then positioned on either side of the two vessel segments 900 and 10'. The jaw members 1010a and 1010b are then compressed about the elastin 10' and the tissue 900 to form a seal.

Alternatively, the elastin biomaterial 10' may be used as reinforcement to conventional circular stapling (See FIG. 8). For example, a conventional circular stapling device 1100 may be configured with a stapler support 1110a, an anvil 1110b, conductive sealing plates 1112a and 1112b, stop members (not shown) and an appropriate force-actuating mechanism (not shown) necessary to seal tissue (as described in detail above). The circular stapler 1100 is then positioned in a normal, conventional fashion about the two vessels segments 900 and 900' with the elastin biomaterial 10' disposed about the vessel segments 900, 900' or between the vessel segments 900, 900' as described above. Prior to activating the stapler 1100, the vessel segments 900, 900' and the elastin biomaterial 10' are fused in accordance with vessel sealing parameters described herein. Once stapled, it is envisioned that the elastin biomaterial 10' will reinforce the stapled anastomosis.

It is also envisioned that a segment of biomaterial 10' and tissue 900 may be directly fused together prior to stapling. For example and as best shown in FIG. 10, a segment of biomaterial 10' and a vessel 900 may both be everted to expose the vessel intimas 10" and 910, respectively. A circular stapler 1100 is then positioned about the two segments 900 and 10' as described above. Prior to activating the stapler 1100, the vessel segment 900 and the biomaterial segment 10' are directly fused in accordance with vessel sealing parameters described herein.

From the foregoing and with reference to the various figure drawings, those skilled in the art will appreciate that certain modifications can also be made to the present disclosure without departing from the scope of the present disclosure. For example, although only an elastin biomaterial 10' has been described herein, it is contemplated that other biomaterials may also be sealed to heal, repair, replace and/or reconstruct tissue, e.g., collagen-based materials, elastin-based materials and fibrin-based materials. Moreover, the biomaterials may be natural, synthetic and/or engineered biomaterials depending upon a particular purpose. The biomaterials may be sealed or fused to tissue substrates, soft tissue (lung, intestine, bowel, blood vessels, muscles, skin, etc.) or other biomaterials utilizing the aforedescribed vessel sealing instruments (or other vessel sealing instruments). As can be appreciated, each particular type of biomaterial may have different sealing parameters and optimum gap and pressure ranges. For example, it is contemplated that Cook Surgical Surgisis Gold porcine collagen biomaterial which is commonly used for hernia repair graft may be fused with fresh porcine peritoneum or fresh porcine fascia or fused with another graft of Surgical Surgisis Gold material to produce a desired surgical result. It is envisioned that Surgical Surgisis Gold may be fused with itself, other biomaterials or other types of human tissues to create various types of aforedescribed grafts, fusions, anastomoses and/or tissue seals. Moreover and as can be appreciated, sheets or patches of Surgical Surgisis Gold may be selectively varied in size, thickness and shape and/or may be formed into molds and scaffolding depending upon the intended purpose for the biomaterial.

Moreover, the RF energy may need to be regulated or controlled (feedback loop, algorithm, closed loop system, etc.) depending upon the type of biomaterial. It is envisioned that various sensors may be employed to closely monitor various tissue parameters (impedance, temperature, moisture, etc.) to optimize the sealing process for each type of biomaterial.

It is also envisioned that the forceps 200, 500 and 700 may be designed such that it is fully or partially disposable depending upon a particular purpose or to achieve a particular result. For example, jaw assembly 400 may be selectively and releasably engageable with the distal end 214 of the shaft 212 and/or the proximal end 216 of shaft 212 may be selectively and releasably engageable with the housing 220 and the handle assembly 230. In either of these two instances, the forceps 200 would be considered "partially disposable" or "reposable", i.e., a new or different jaw assembly 400 (or jaw assembly 400 and shaft 212) selectively replaces the old jaw assembly 400 as needed.

It is also envisioned that the jaws members 410 and 420 may closed in a tip-based or heel-based fashion. Alternatively, the jaw members 410 and 420 may close in a parallel or independently floating (with respect to parallel) fashion. It is also contemplated that optimizing hydration levels of a biomaterial prior to sealing may be desired, e.g., pressing the biomaterial with gauze. This may be included as an additional step in the sealing process.

As mentioned above, for certain applications, it may be desirable to use the biomaterial with a supporting material having strong mechanical properties, e.g., polymers, such as woven polyethylene terepthalate (Dacron), teflon, polyolefin copolymer, polyurethane polyvinyl alcohol, polyacrylic or other polymers.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of fusing biomaterial and tissue using radiofrequency energy, comprising the steps of:
   providing a vessel sealing instrument having opposing jaw members which are movable relative to one another to compress tissue therebetween, the vessel sealing instrument having at least one stop member affixed thereto for regulating the distance between opposing jaw members;

providing a biomaterial by extracting collagen from the biomaterial and confirming the absence of collagen from the biomaterial;

positioning the biomaterial in abutting relation to tissue;

grasping the biomaterial and tissue between the jaw members;

compressing the biomaterial and tissue between the jaw members under a working pressure within the range of about 3 kg/cm$^2$ to about 16 kg/cm$^2$; and energizing the jaw members with radiofrequency energy to effectively fuse the biomaterial and the tissue such that the biomaterial and the tissue reform into a single, fused mass.

2. A method of fusing biomaterial and tissue using radiofrequency energy according to claim 1 wherein the biomaterial of the providing step is elastin.

3. A method of fusing biomaterial and tissue using radiofrequency energy according to claim 1 wherein the stop member of the providing step regulates the distance between opposing jaw members within the range of about 0.004 inches to about 0.010 inches.

4. A method of fusing biomaterial and tissue using radiofrequency energy according to claim 1 wherein the biomaterial is fused between two tissue segments.

5. A method of fusing biomaterial and tissue using radiofrequency energy according to claim 1 wherein the biomaterial is tubular in shape.

6. A method of fusing biomaterial and tissue using radiofrequency energy, comprising the steps of:

providing a circular stapling instrument having a stapler support member which supports an array of staples and an opposing anvil, the support member being movable relative to the anvil to compress tissue therebetween, each of the stapler support member and the anvil having electrically conductive sealing surfaces;

providing a biomaterial by extracting collagen from the biomaterial and confirming the absence of collagen from the biomaterial;

everting an end of a segment of biomaterial;

positioning the everted end of the biomaterial in abutting relation to an everted tissue end such that the respective intimae of the everted biomaterial and the tissue oppose one another;

compressing the biomaterial and tissue between the stapler support member and the anvil under a working pressure within the range of about 3 kg/cm$^2$ to about 16 kg/cm$^2$;

energizing the support member and the anvil with radiofrequency energy to effectively fuse the biomaterial and the tissue such that the tissue and the biomaterial reform into a single, fused mass; and actuating the circular stapling instrument to fire the staples through the biomaterial and tissue and against the anvil.

7. A method of fusing biomaterial and tissue using radiofrequency energy according to claim 6 wherein the biomaterial of the providing step is elastin.

8. A method of fusing biomaterial and tissue using radiofrequency energy according to claim 6 wherein the stop member of the providing step regulates the distance between opposing jaw members within the range of about 0.004 inches to about 0.010 inches.

9. A method of fusing biomaterial and tissue using radiofrequency energy, comprising the steps of:

providing a circular stapling instrument having a stapler support member which supports an array of staples and an opposing anvil, the support member being movable relative to the anvil to compress tissue therebetween, each of the stapler support member and the anvil having electrically conductive sealing surfaces;

providing a biomaterial by extracting collagen from the biomaterial and confirming the absence of collagen from the biomaterial;

everting the ends of two tissue segments to expose tissue intimae;

positioning at least one segment of biomaterial between the everted ends of the two tissue segments;

compressing the two tissue segments and the biomaterial between the stapler support member and the anvil under a working pressure;

energizing the support member and the anvil with radiofrequency energy to effectively fuse the biomaterial and the two tissue segments such that the two tissue segments and the biomaterial reform into a single, fused mass; and actuating the circular stapling instrument to deform the staple through the biomaterial and tissue and against the anvil.

* * * * *